(12) United States Patent
Sholev et al.

(10) Patent No.: US 12,201,274 B1
(45) Date of Patent: Jan. 21, 2025

(54) SURGICAL PORT ADD-ON AND ADAPTOR FOR A SURGICAL PORT

(71) Applicant: Scopix Ltd., Amikam (IL)

(72) Inventors: Mordehai Sholev, Amikam (IL); Asaf Sholev, Amikam (IL)

(73) Assignee: Scopix Ltd., Amikam (IL)

( * ) Notice: Subject to any disclaimer, the term of this patent is extended or adjusted under 35 U.S.C. 154(b) by 0 days.

(21) Appl. No.: 18/219,685

(22) Filed: Jul. 9, 2023

(51) Int. Cl.
| | |
|---|---|
| A61B 1/00 | (2006.01) |
| A61B 1/12 | (2006.01) |
| A61B 1/32 | (2006.01) |
| A61B 17/34 | (2006.01) |
| A61M 13/00 | (2006.01) |
| A61B 17/00 | (2006.01) |

(52) U.S. Cl.
CPC ............ A61B 1/126 (2013.01); A61B 1/32 (2013.01); A61B 17/3415 (2013.01); A61M 13/003 (2013.01); A61B 2017/00477 (2013.01)

(58) Field of Classification Search
CPC ....... A61B 1/126; A61B 1/32; A61B 17/3415; A61B 17/34; A61B 2017/00477; A61B 2017/345; A61M 13/003; A61M 29/00
USPC ......................................................... 600/114
See application file for complete search history.

(56) References Cited

U.S. PATENT DOCUMENTS

| | | |
|---|---|---|
| 6,354,992 B1 | 3/2002 | Kato |
| 8,047,215 B1 | 11/2011 | Sasaki |
| 8,535,220 B2 | 9/2013 | Mondschein |
| 8,888,689 B2 | 11/2014 | Poll et al. |
| 8,945,155 B2 | 2/2015 | Gordin et al. |
| 2006/0293559 A1* | 12/2006 | Grice, III ............... A61B 1/122 600/102 |
| 2007/0260273 A1* | 11/2007 | Cropper ............ A61B 1/00087 606/185 |
| 2009/0240111 A1 | 9/2009 | Kessler et al. |
| 2009/0281478 A1 | 11/2009 | Duke |
| 2014/0215736 A1 | 8/2014 | Gomez |
| 2014/0318582 A1 | 10/2014 | Mowlai-Ashtiani |
| 2015/0080660 A1 | 3/2015 | Gomez et al. |
| 2015/0282695 A1 | 10/2015 | Tay |
| 2016/0135673 A1* | 5/2016 | Miller .................... A61B 1/126 15/244.4 |
| 2018/0256283 A1 | 9/2018 | Rosenbaum et al. |
| 2020/0054337 A1* | 2/2020 | Sgroi, Jr. ............. A61B 17/072 |

(Continued)

FOREIGN PATENT DOCUMENTS

EP 3906836 A1 11/2021

OTHER PUBLICATIONS

United States Patent and Trademark Office, Non-Final Office Action for U.S. Appl. No. 18/540,218, mailed Apr. 4, 2024, 35pp.

(Continued)

Primary Examiner — Timothy J Neal
Assistant Examiner — James Edward Boice
(74) Attorney, Agent, or Firm — The Roy Gross Law Firm, LLC; Roy Gross

(57) ABSTRACT

The present invention discloses to surgical port add-on, an adaptor, modules and methods thereof for producing and using a surgical port especially adapted for cleaning surgical tools operable in a body cavity. The invention also discloses a surgical port add-on, an adaptor, modules and methods thereof an adaptor that can be pertaining to the attached in or on a trocar and for use of the same d for cleaning the lens and light source of an endoscope.

19 Claims, 28 Drawing Sheets

(56) References Cited

U.S. PATENT DOCUMENTS

2020/0060536 A1    2/2020   Rylander
2020/0375444 A1*  12/2020   Coffeen ............. A61B 1/00135
2022/0361740 A1*  11/2022   Fang ...................... A61B 1/126
2022/0370096 A1   11/2022   Sholev

OTHER PUBLICATIONS

International Search Report of PCT/IL2024/050669 Completed Nov. 10, 2024; Mailed Nov. 10, 2024 4 pages.
Written Opinion of PCT/IL2024/050669 Completed Nov. 10, 2024; Mailed Nov. 10, 2024 4 pages.

\* cited by examiner

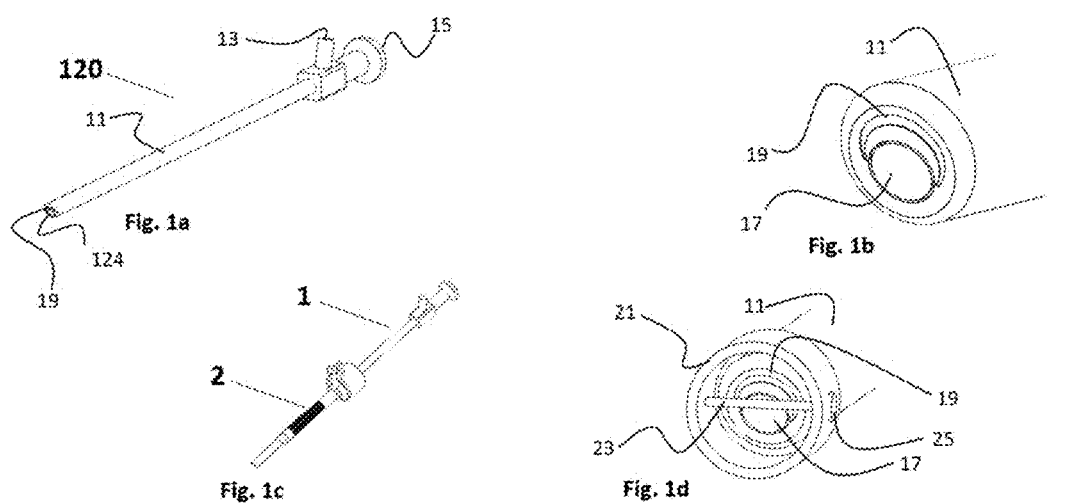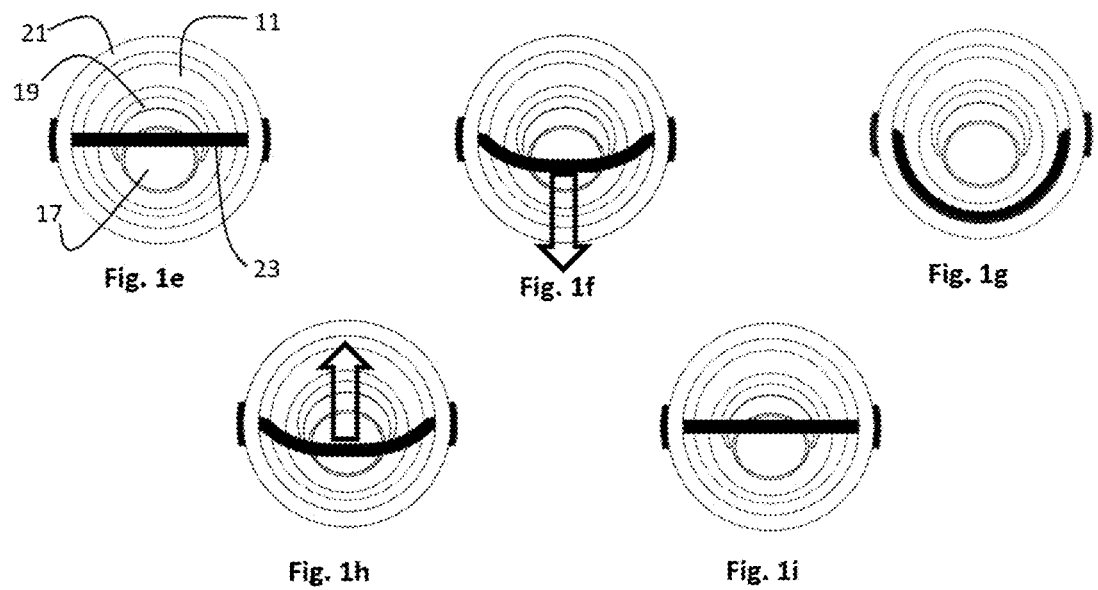

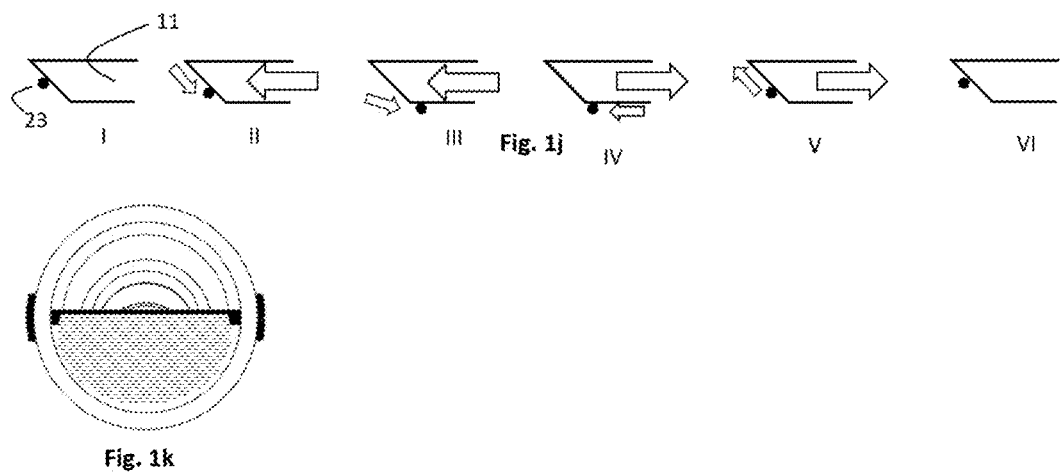
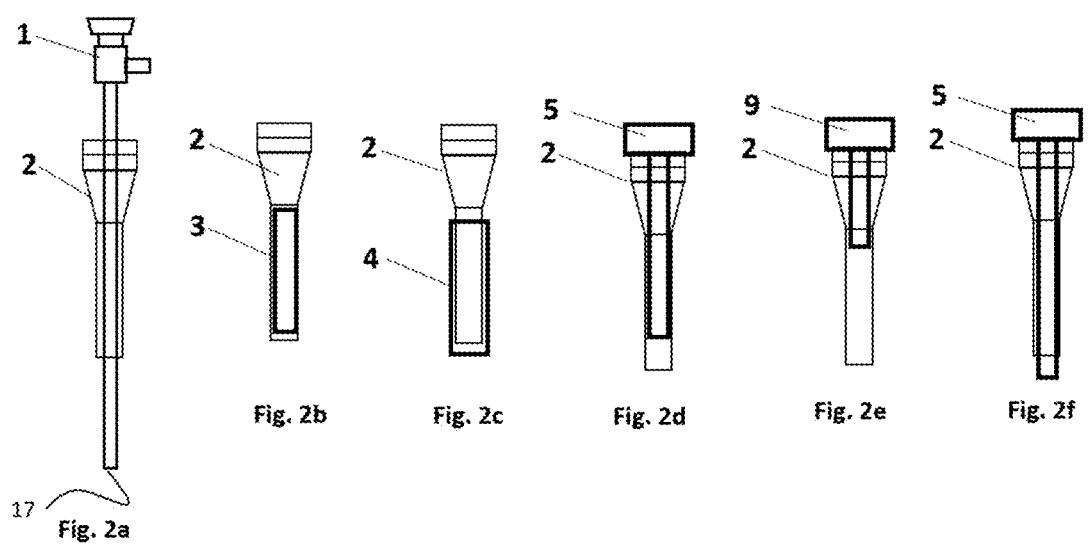
Figure 2

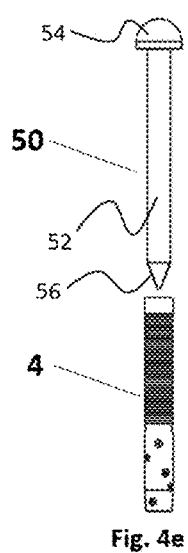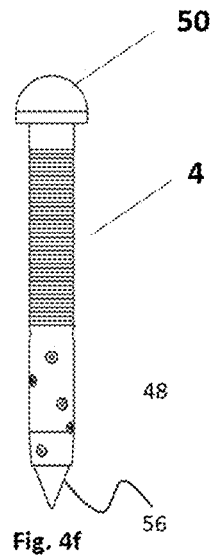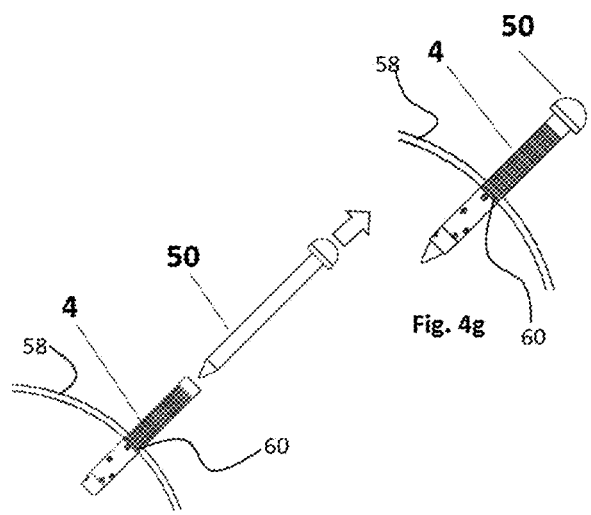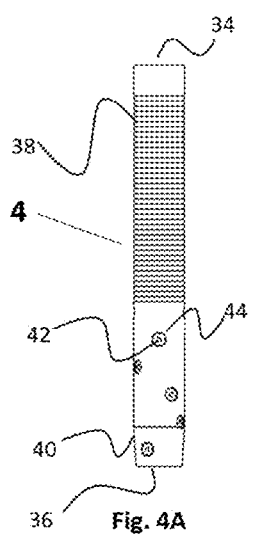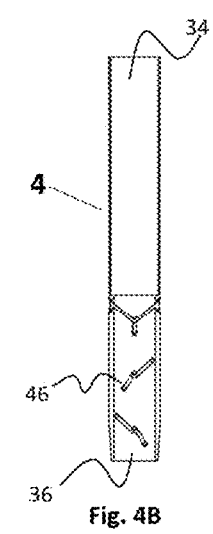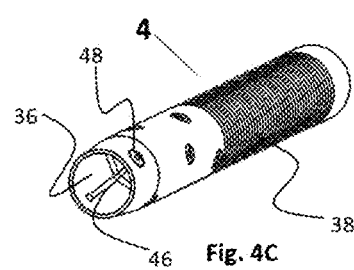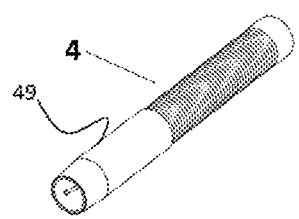

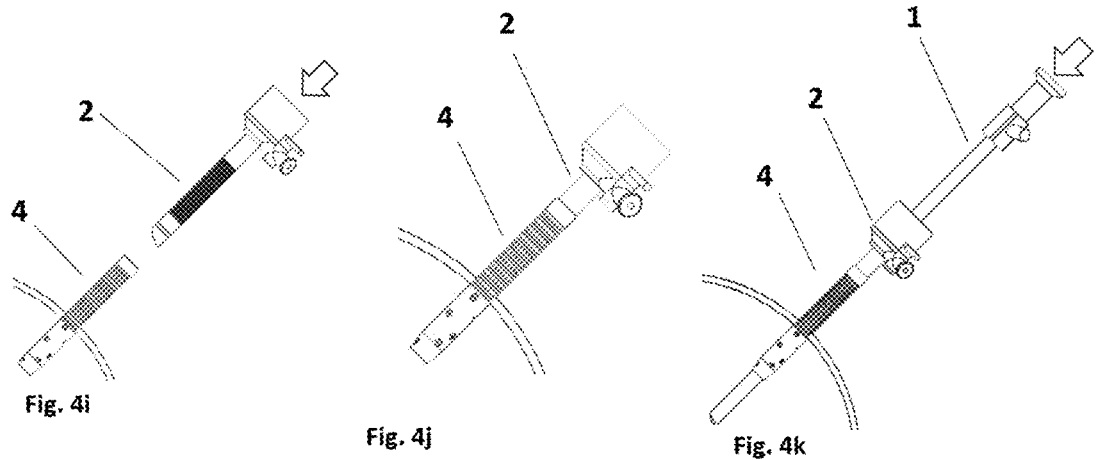
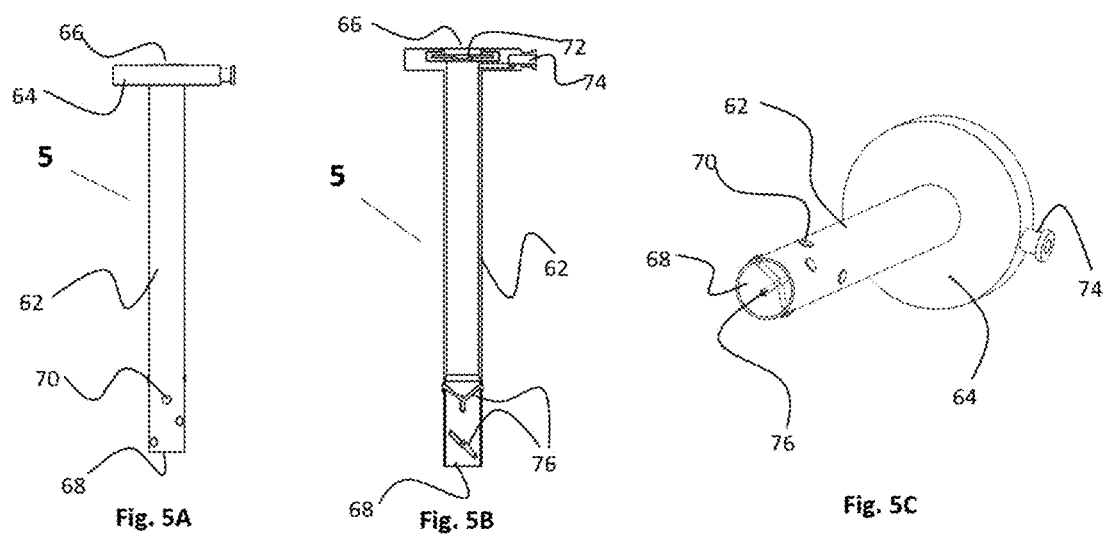

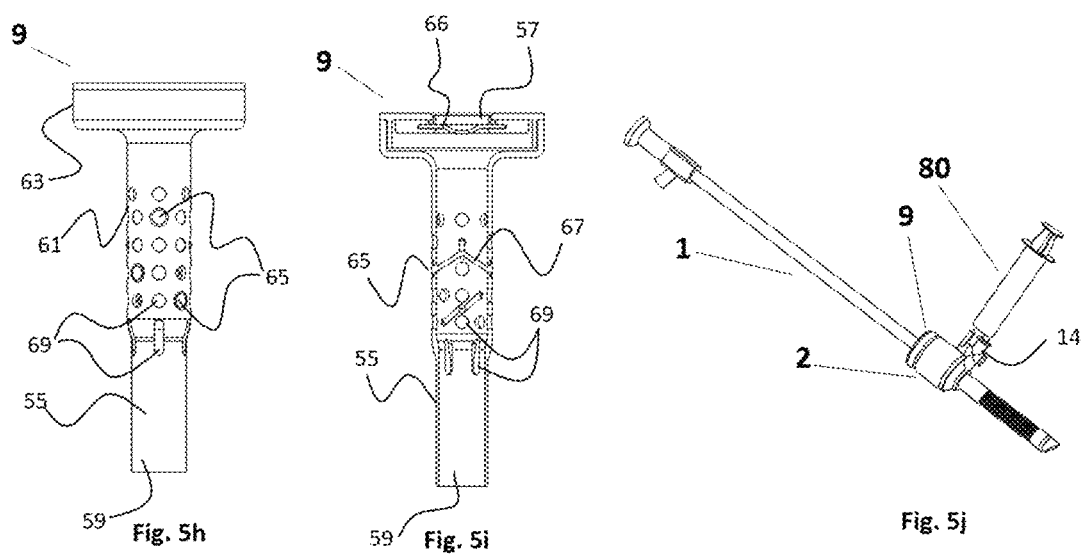
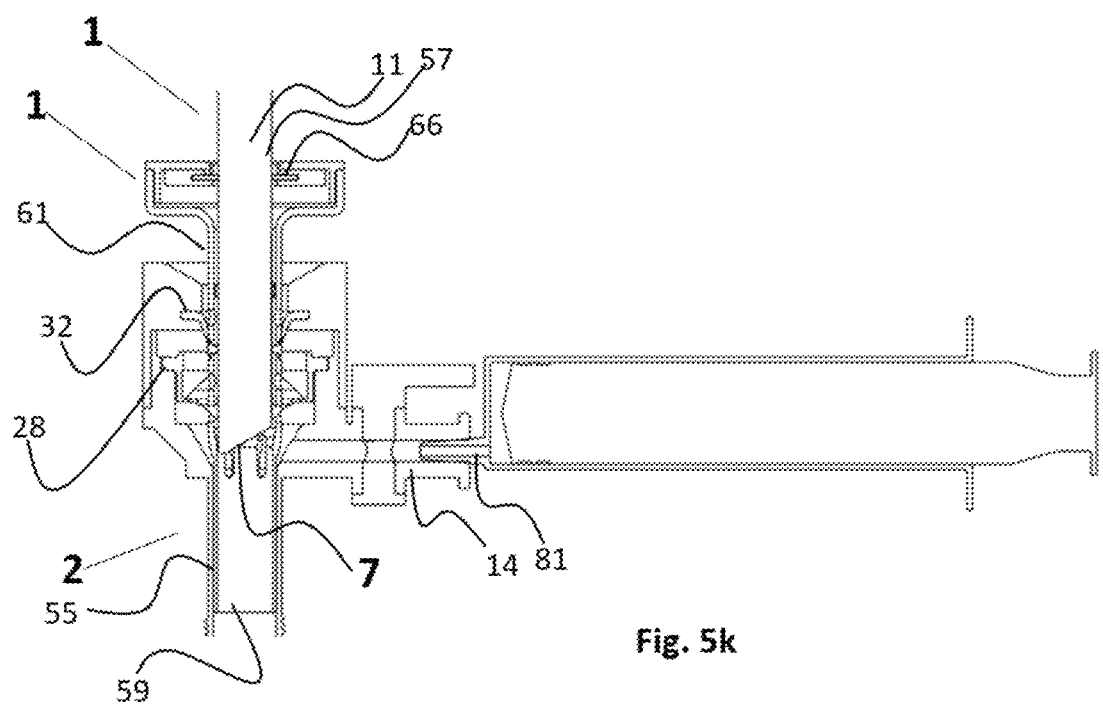

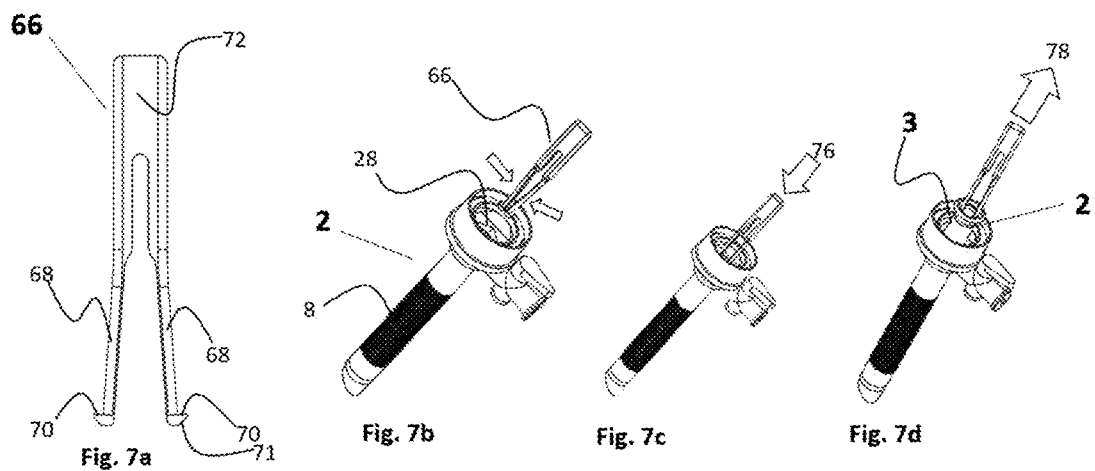
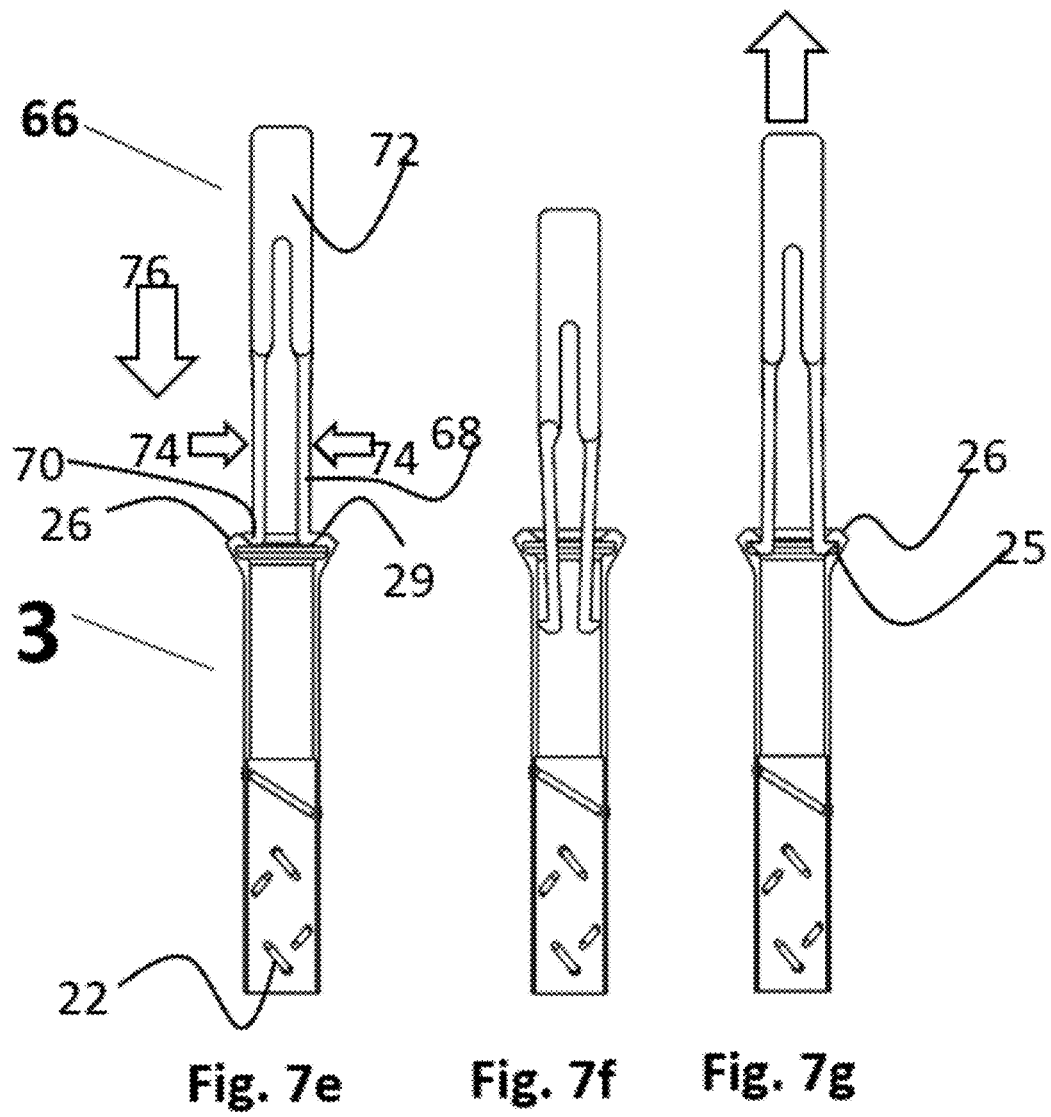
Fig. 7a  Fig. 7b  Fig. 7c  Fig. 7d
Fig. 7e  Fig. 7f  Fig. 7g

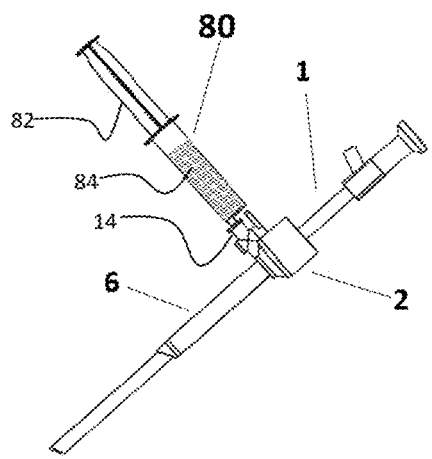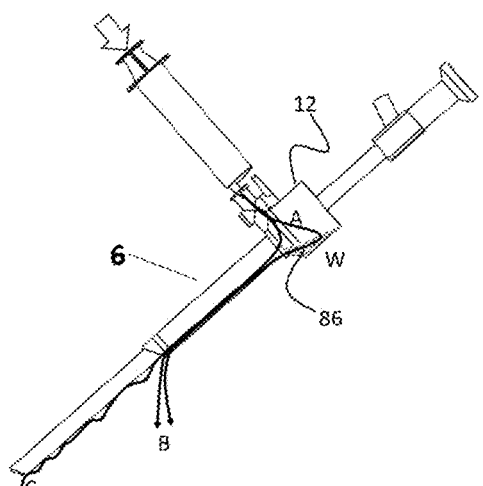
Fig. 8a
Fig. 8b
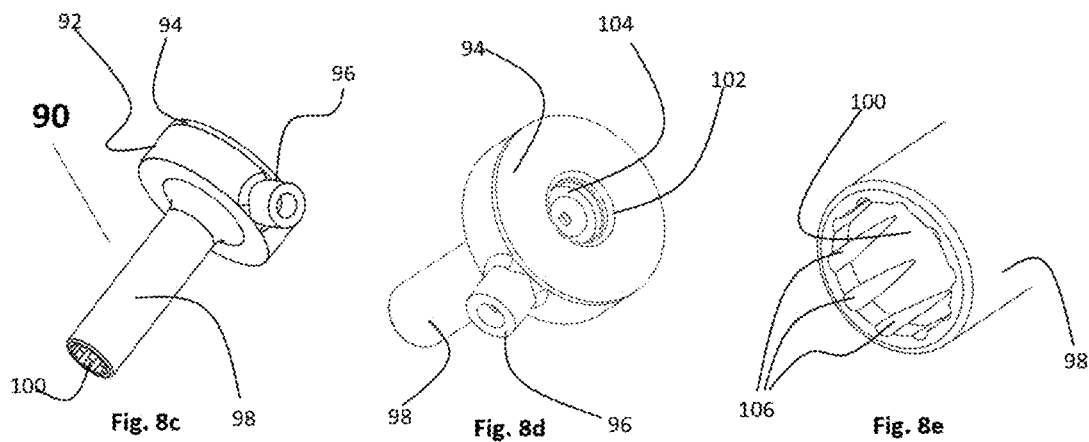
Fig. 8c
Fig. 8d
Fig. 8e

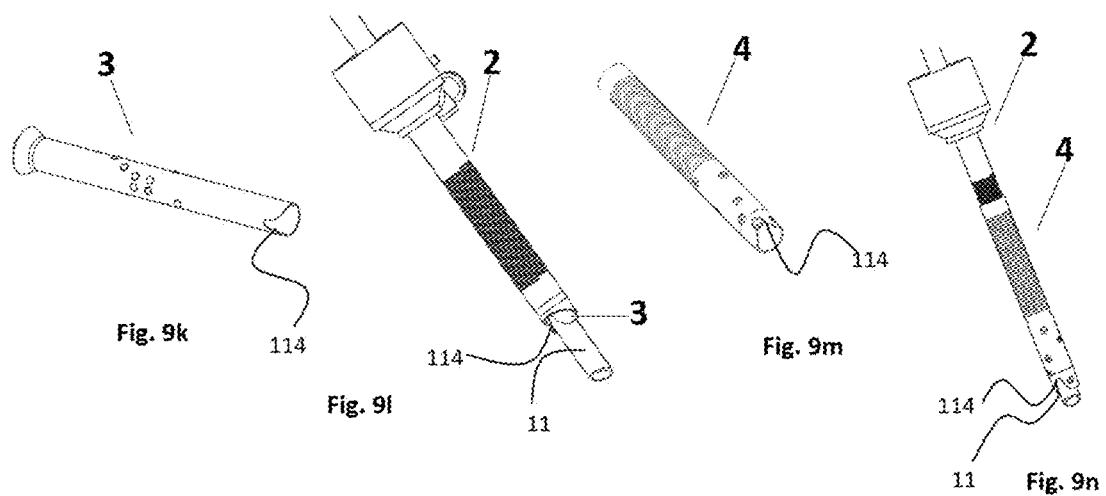

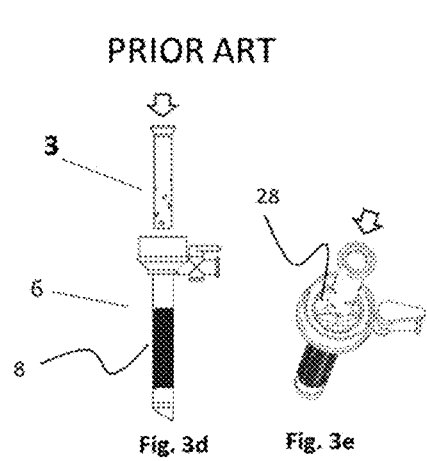
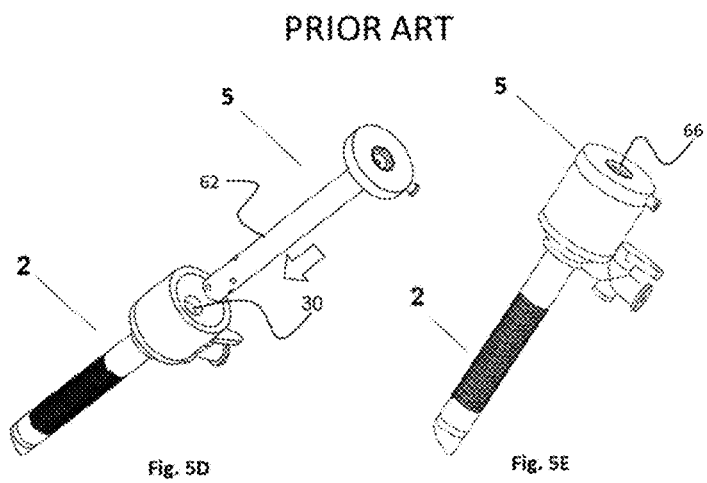
Fig. 11c
Fig. 11d
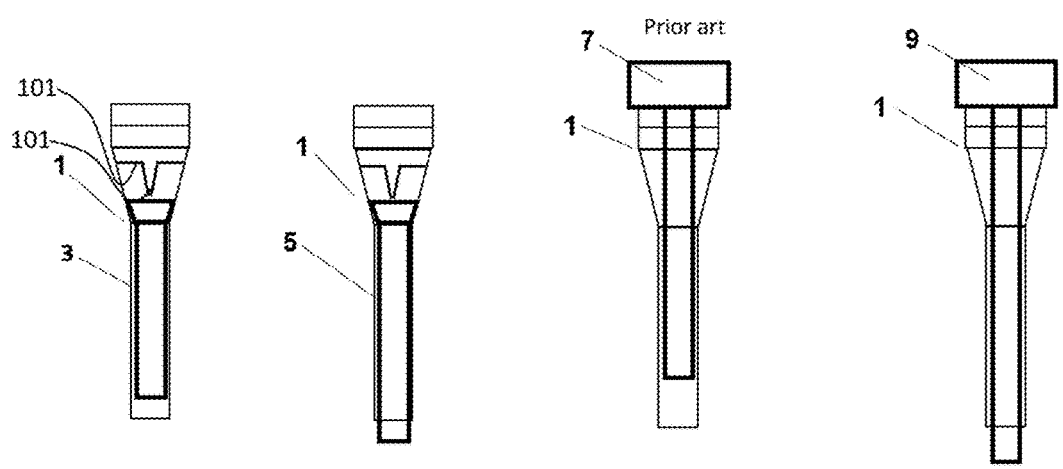
Fig. 12a  Fig. 12b  Fig. 12c  Fig. 12d

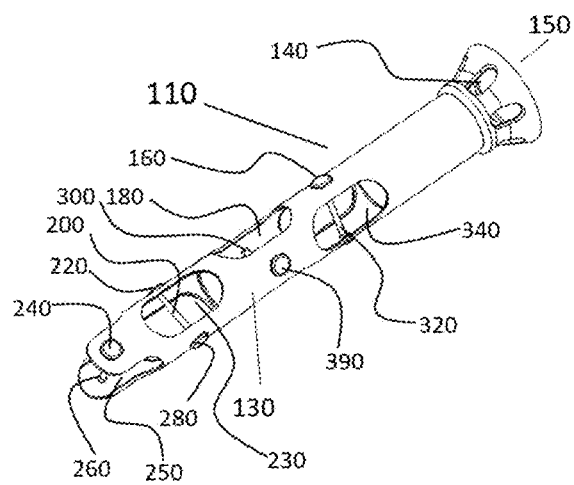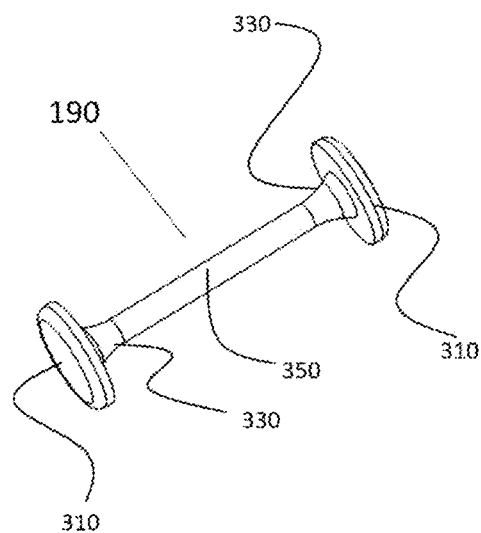
Fig. 13a  Fig. 13b
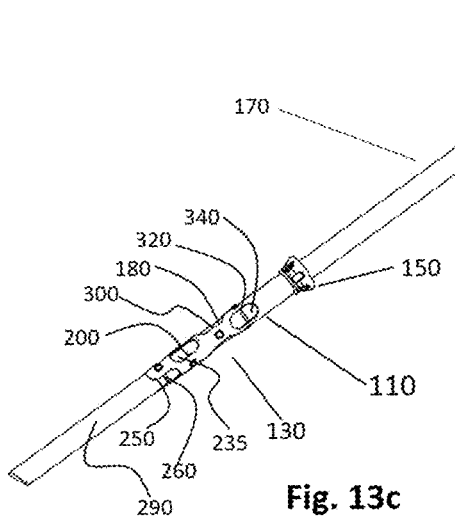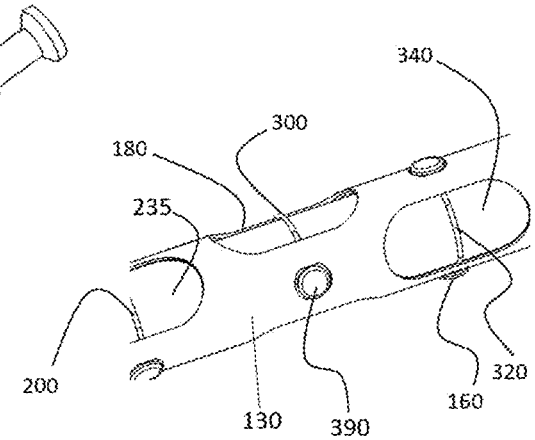
Fig. 13c  Fig. 13d

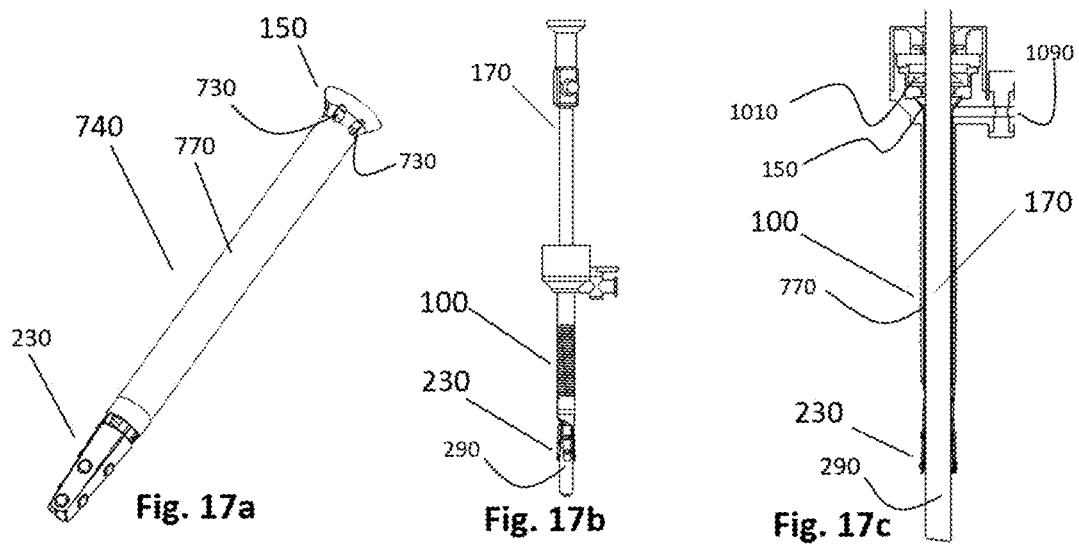

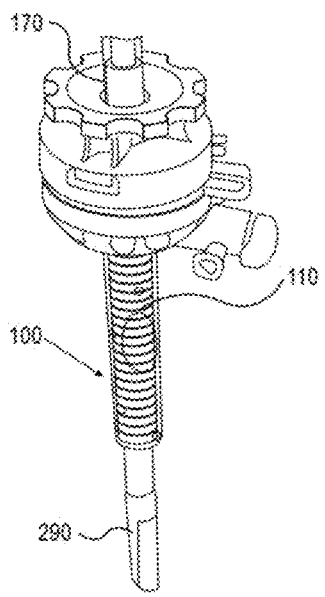
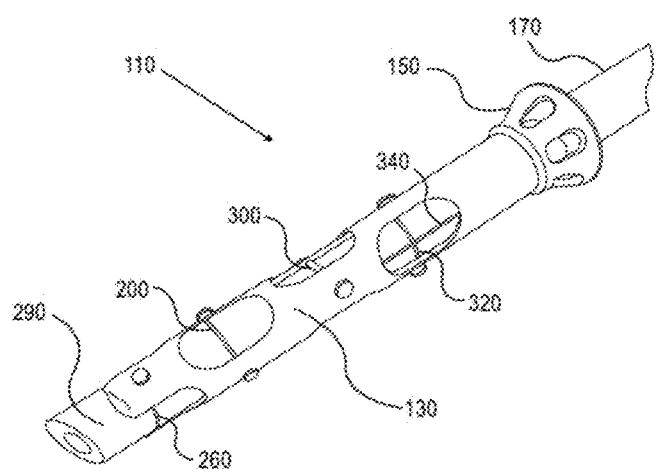
Fig. 18a					Fig. 18b
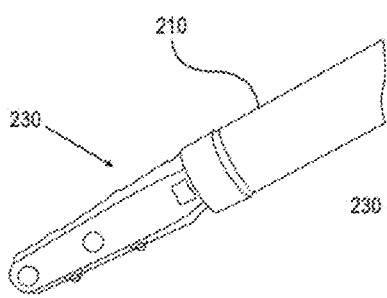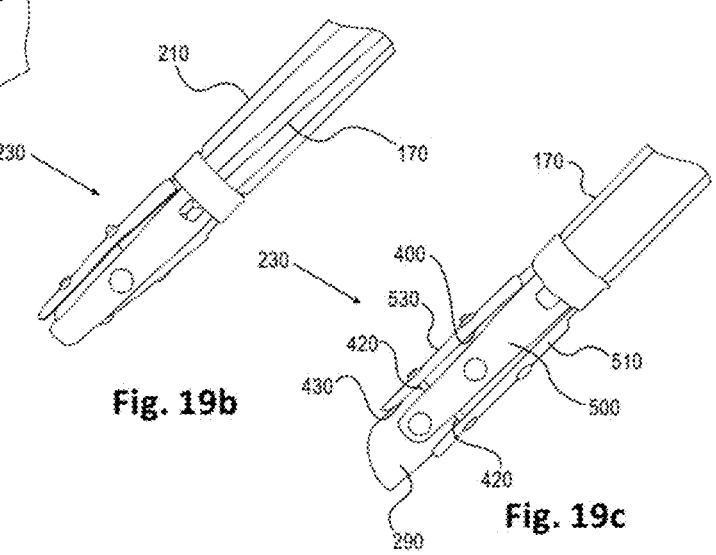
Fig. 19a			Fig. 19b			Fig. 19c

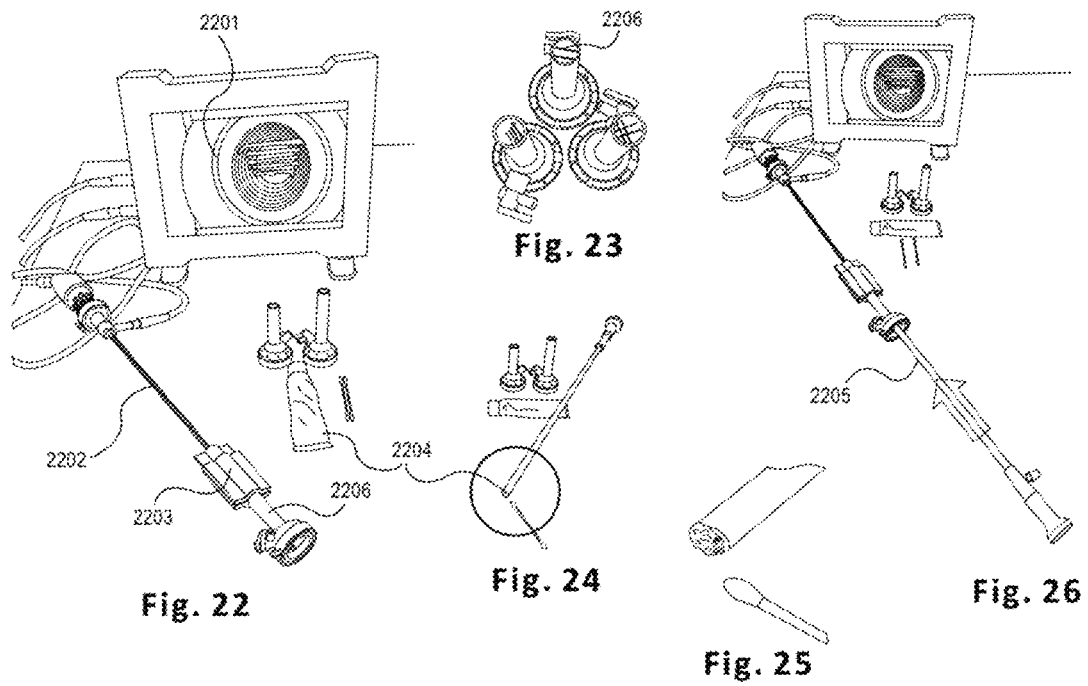
Fig. 23
Fig. 22  Fig. 24  Fig. 26
Fig. 25
Parallel wide   Parallel narrow   Horizontal grid   Horizontal grid + X   cross
Figure 27
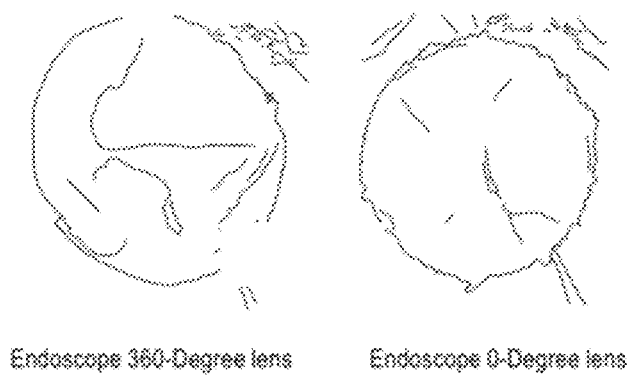
Endoscope 360-Degree lens    Endoscope 0-Degree lens
Figure 28

SURGICAL PORT ADD-ON AND ADAPTOR FOR A SURGICAL PORT

FIELD AND BACKGROUND OF THE INVENTION

The present invention generally relates to surgical port add-on, an adaptor, modules and methods thereof for producing and using a surgical port especially adapted for cleaning surgical tools operable in a body cavity. Embodiments of the present invention relate to surgical port add-on, an adaptor, modules, and methods thereof an adaptor that can be pertaining to the attached in or on a trocar and for use of the same d for cleaning the lens and light source of an endoscope.

A minimally invasive procedure has less operative trauma, post-operative complications, and adverse effects than an equivalent open surgery. Laparoscopic surgery for example, decreases post-operative patient discomfort and healing while reducing hospitalization time and costs.

Minimally invasive surgeons rely on minimally invasive instruments operable from outside the body to manipulate target tissues within a body. In order to accurately guide the tools and correctly perform the procedure, surgeons utilize an intrabody scope (endoscope) to visualize the operative end of the tools and the target tissues. Some procedure (e.g., diagnostic procedures) can be performed using an endoscope alone.

During a procedure, tissue, blood, and other body fluids can attach to the objective lens of the endoscope and obscure vision. This requires the surgeon to remove the endoscope from the body cavity and clean the objective lens. Some operative procedures require frequent removal of the endoscope for cleaning considerably extending the time of the procedure and increasing the likelihood of infection due to device removal and reintroduction.

Numerous solutions to this problem have been proposed, see for example, U.S. Pat. Nos. 6,354,992, 8,047,215, 8,535,220, 8,888,689, 8,945,155, US20090240111, US20140318582, US20150080660; however, there is still a need for an easy, inexpensive, and effective solution for endoscopic lens fouling.

SUMMARY OF THE INVENTION

According to one aspect of the present invention there is provided a port adaptor for a surgical port comprising an adaptor body and at least one elastomeric band stretched across a diameter of an internal lumen of the adaptor body, wherein the adaptor body includes elements for attaching it to a surgical port.

According to embodiments of the present invention the adaptor comprises a plurality of the elastomeric band arranged in a grate pattern.

According to embodiments of the present invention the adaptor comprises a plurality of the elastomeric band arranged in a crossing pattern.

According to embodiments of the present invention the at least one elastomeric band is made from rubber or silicone.

According to embodiments of the present invention the adaptor body is sized and configured for placement in a lumen of a trocar, around the trocar or at the proximal opening of the trocar.

According to another aspect of the present invention there is provided a device for cleaning a trocar cannula comprising a housing with an opening for attachment over a trocar cannula, the opening being for delivering a fluid to the cannula wherein an inner surface of the opening includes a plurality of circumferentially positioned longitudinal grooves for increasing a pressure of a fluid delivered through the opening.

According to another aspect of the present invention there is provided a cannula for guiding an endoscope comprising a cannula body having proximal and distal openings, wherein the distal opening includes a contoured cutout for facilitating draining of a liquid injected through the proximal opening when the endoscope is positioned within the cannula.

According to embodiments of the present invention the cannula body forms a part of a trocar.

According to embodiments of the present invention, an endoscope cleaning device comprises a median tube, a proximal cap and a distal end cleaning mechanism. The median tube is having proximal end connected to proximal cap and distal end connected to said cleaning head mechanism. The median tube has outer diameter configured for insertion of said cleaning device into the cannula of a trocar, through the proximal opening of said trocar.

According to embodiments of the present invention, in the endoscope cleaning device defined above, the median tube has holes located in said median tube for delivering gas for inflating procedure site and injecting saline into said median tube for cleaning the distal cleaning head.

According to embodiments of the present invention, in the endoscope cleaning device defined above, the holes are located under the duck valve of a trocar, when said endoscope cleaning device is installed in trocar.

According to embodiments of the present invention, a method of cleaning surgical tools in a body cavity comprises steps of obtaining an endoscope cleaning device comprising a median tube, a proximal cap and a distal end cleaning mechanism. The median tube is having proximal end connected to proximal cap and distal end connected to said cleaning head mechanism. The median tube has outer diameter configured for insertion of said cleaning device into the cannula of a trocar, through the proximal opening of said trocar. The method further comprising step of pushing cleaning device into proximal end of the trocar until arms engage with the proximal cap of trocar.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 1a-1k illustrate use of a port adaptor having a single cleaning cord to wipe and clean a distal lens and light source of an endoscope fitted therein;

FIGS. 2a-2f illustrate several embodiments of the port adaptor of the present invention;

FIGS. 4a-4k illustrate an embodiment of the port adaptor of the present invention that is installed around the trocar cannula;

FIGS. 5a-5k illustrate an embodiment of the port adaptor of the present invention that is installed at a proximal opening of a trocar;

FIGS. 7a-7g illustrates a tool for retrieving a port adaptor from a trocar;

FIGS. 8a-8k illustrate a device for cleaning the inside surface of trocar;

FIGS. 11a-11d are prior art illustrations;

FIGS. 12a-12d illustrate schematically some of possible embodiments of the present inventions, whereas FIG. 12C illustrates the prior art;

FIGS. 13a-13d illustrate one embodiment of the where the endoscope lens cleaning device is installed in the trocar cannula;

FIGS. 17a-17c illustrate another embodiment of the present invention where the endoscope lens cleaning device is installed in the trocar cannula;

FIGS. 18a-18b are prototype photos of one embodiment of the invention, as described in FIGS. 13a-d;

FIGS. 19a-19c are prototype photos of another embodiment of the invention, as described in FIGS. 14a-i;

FIGS. 22-30 are photos and schematic illustration of another embodiments, provided as an example of the efficiency of the technology disclosed in the present invention.

DESCRIPTION OF THE PREFERRED EMBODIMENTS

Figure 3A:
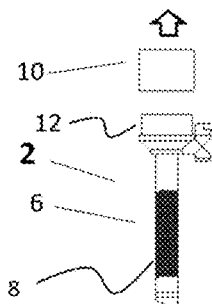
FIGS. 3a-3j illustrate an embodiment of the port adaptor of the present invention that is installed within the trocar cannula.

The present invention discloses surgical port add-on, an adaptor, modules and methods thereof for producing and using a surgical port especially adapted for cleaning surgical tools operable in a body cavity. The invention also discloses a surgical port add-on, an adaptor, modules and methods thereof an adaptor that can be pertaining to the attached in or on a trocar; and means and methods for cleaning the lens and light source of an endoscope, e.g., during a minimally invasive surgical procedure. The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Fouling of an objective lens of an endoscope is a problem frequently encountered during a minimally invasive procedure. Since such fouling can reduce the field of view and or image quality obtained from the endoscope, a surgeon must remove the endoscope from the body and manually clean the objective lens several times in a procedure thereby complicating the procedure, increasing operative time and the chances of infection.

Several solutions have been proposed to this frequently encountered problem, ranging from cleaning sheaths to heating and treatment with anti-fog solutions.

While reducing the present invention to practice, the present inventor devised a port adaptor that includes a wiper assembly constructed from one or more elastic bands positioned across the lumen of the adaptor. As is further described hereinbelow, the port adaptor can be fitted in or around the surgical port anywhere along its length.

Thus, according to one aspect of the present invention there is provided a port adaptor that can be used with a surgical port for cleaning of a medical device e.g., a surgical instrument such as an endoscope.

As used herein the term "surgical port" refers to any device that can be used to provide surgical access to a body cavity through a tissue surrounding the body cavity. An example of a port is a trocar that is made up of a cannula, a seal and optionally an awl/obturator (for piercing tissue). Trocars are placed through the abdomen during laparoscopic surgery and function as a portal for the subsequent placement of surgical instruments such as an endoscope.

As used herein, the term "endoscope" refers to a device used for observation within a body cavity/lumen. A typical endoscope includes a rigid or flexible shaft approximately 300-500 mm in length, with an outer diameter of 3 mm to 12 mm. The shaft includes an objective lens at a distal end and an eyepiece or camera at the proximal end. The objective lens is optically coupled to the eyepiece or camera via light-transmitting glass fibers and/or rod lenses. The endoscope can also include a light source for illuminating the body cavity.

As used herein the terms "about" and ""approximately" interchangeably refers to +10% of the defined measure.

Thus, according to one aspect of the present invention there is provided a surgical port adaptor (also referred to herein as "port adaptor") for a surgical port. The adaptor includes an adaptor body and at least one elastomeric band (e.g., 1-10) stretched across a diameter of an internal lumen of the adaptor body (and arranged in various patterns as is described hereinunder). The port adaptor is configured for attachment to a surgical port (e.g., trocar) and as such includes elements for engaging a lumen of a trocar, an outer surface or the proximal or distal ends of the trocar.

Referring now to the drawings, FIGS. 1a-10d illustrate various embodiments of the port adaptor of the present invention.

FIGS. 1a-g illustrate use of single cleaning cord to wipe and clean the endoscope distal lens and light source.

FIG. 1a demonstrates an endoscope with a structure commonly used to preform minimal invasive surgical procedures. Endoscope 1 has shaft 11 with diameters of 3-12 mm, and length from 100-500 mm. The shaft contains usually optic fibers that connects proximal input connector 13 to the distal end 19 of shaft 11. Camera connector 15 located at the proximal end of endoscope 1, receives the image from the surgical site via system of lenses located along shaft 11 to distal lens 17 located at the distal end of shaft 11.

FIG. 1b is a magnified image of the distal end of endoscope 11 showing lens 17 and light source 19.

FIG. 1c demonstrates passing of endoscope 1 through trocar 2 as used in minimal invasive surgical procedures.

FIG. 1d illustrates a simplified port adaptor that will be explained in detail in the next Figures. Distal end of shaft 11 of endoscope 1 is in short tube 21. Short tube 21 contains a single elastic cord 23 that pass inside tube 21. In this figure for the purpose of explanation, cord 23 passes through the center of tube 21. FIGS. 6a-m illustrate in detail other possible embodiment using multiple cleaning cords in various pattern and spatial arrangements.

While pushing the distal end of endoscope 1 through tube 21, the endoscope distal end with lens 17 and light source 19 must contact elastic cord 23 and push it away (sideways) from shaft 11 of endoscope 1. While the distal end of endoscope 1 pushes elastic cord 23, cord 23 wipes part of the distal end of endoscope 1 and may remove fog, blood, or any material from the endoscope distal end. If elastic cord slides over a portion of lens 17 or light source 19 then some material might be left on the lens or light source. To clean the whole area of the distal end of the endoscope, the surgeon may pull the endoscope back to the proximal end of tube 21, rotate the endoscope along the long axis of shaft 11, and push the distal end of endoscope 1 against the elastic cord, causing the cord to wipe different area of the distal end of the endoscope. Repeating of this process for few times may clean the whole area of the distal end of endoscope 1, enabling the surgeon to view the surgical site clearly. It should be noted that while pulling the endoscope back to the proximal end of tube 21, the elastic cord 23 also wipes the distal end of endoscope due the elastic forces the cord to retrieve its original position and elastic state.

FIGS. 1e-i are frontal views demonstrating the path of elastic cord over the endoscope distal end. FIG. 1e shows the elastic cord 23 in its initial position at the center of tube 21. FIG. 1f shows elastic cord 23 stretched while moving down and wiping part of lens 17 and part of source light 19. FIG. 1g show elastic cord under shaft 11 of endoscope 1, allowing the surgeon to push the endoscope in a preferred position.

FIG. 1h shows elastic cord 23 moves up wiping part of the distal end of the endoscope while the surgeon pulls the endoscope over the position of elastic cord 23. FIG. 1i show the elastic cord 23 in its initial position at the center of tube 21.

FIG. 1j illustrates a side view of the wiping movement of elastic cord 23 while the distal end of shaft 11 is pushed and pulled in the tube against and over elastic cord 23.

FIG. 1k shows an approximation of the area wiped by single elastic cord 23, while the endoscope is pushed or pulled over elastic cord 23, as was illustrated in FIGS. 1. e-j.

FIGS. 2a-fe illustrate some of possible embodiments of the endoscope port adaptor.

FIG. 2a illustrates a trocar 2 with endoscope 1 passing through the trocar cannula.

FIG. 2b illustrates trocar 2 with port adaptor 3 installed in the trocar cannula, as is described hereinbelow with reference to FIGS. 3a-g.

FIG. 2c illustrates trocar 2 with port adaptor 4 installed on the trocar cannula, covering the cannula distal opening as is described hereinbelow with reference to FIG. 4a-k.

FIGS. 2d-f illustrates trocar 2 with ports adaptors 5,9J installed through the trocar proximal opening cannula, as is described hereinbelow with reference to FIG. 5a-k. these embodiments may be useful for trocars with unremovable caps.

FIGS. 3a-j illustrate one embodiment of the present invention where the port adaptor 3 is installed in the trocar 2 cannula.

FIG. 3a illustrates trocar 2 where its proximal cap 10 being removed from the main body 6. Proximal cap 10 usually contains at least one valve that prevent the gas used to inflate the patient body cavities from leaking, as may see also in FIG. 3h and FIG. 3i. Main body 6 may contain beside cannula 8, additional sealing valve 28, placed at the proximal opening of main body 6. Main body 6 may also contain spigot 14, used usually for delivering the gas flow into the patient body cavities. Spigot 14 may be used also for spraying saline into main body 6, to rinse the lower part of valve 28 and the inner surface of cannula 8, when endoscope 1 is being removed out of trocar 2, when the surgeon wishes to clean lens 17 of endoscope 1.

Figure 3B:
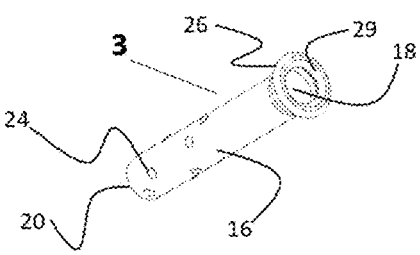
Figure 3C:
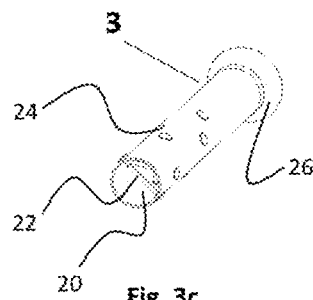
Figure 3D:
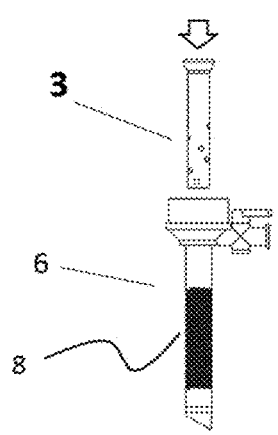
Figure 3E:
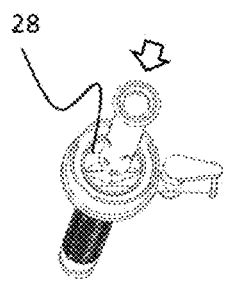
Figure 3F:
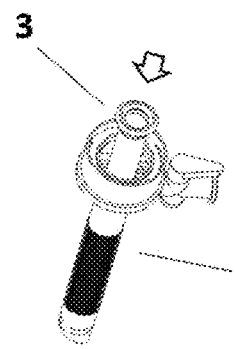
Figure 3G:
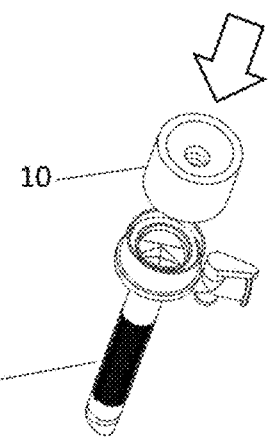

FIGS. 3b-c illustrate port adaptor 3 that can be installed in trocar cannula 8.

Port adaptor includes a thin tube (cannula) with proximal opening 18 and distal opening 20. Proximal opening has bulge 26 used for preventing port adaptor from advancing into cannula 8 when endoscope 1 is pushed through port adaptor cannula 16, or from being pulled out of valve 28 when endoscope 1 is pulled through port adaptor cannula 16. Bulge 26 also serve as part of mechanism that enables the surgeon to pull port adaptor out of trocar main body 6, when the surgeon wishes to clear cannula 8, as is described hereinbelow with reference to FIGS. 7a-h.

FIG. 3c also demonstrates cleaning cords 22 shown through opening 20 of port adaptor 3. In FIG. 3c cleaning cords pass through the walls of cannula 16, while bulges 24 keep the cords tensed in their position.

FIGS. 3d-g illustrate the installing process of port adaptor in cannula 8 of trocar 2. After cap 10 was removed from trocar main body 6 as shown in FIG. 3a. the surgeon simply push port adaptor 3 into cannula 8 through valve 28 as may be seen in FIGS. 3d-f. After device proximal opening 18 with bulge 26 are pushed completely under valve 28, the surgeon may attach cap again to the trocar main body 6, as may be seen in FIG. 3g.

The positioning of port adaptor distal to valve 28, ensures that the functionality of the valve 28 is maintained, preventing leaking of gas from the patient body while endoscope 1 is being removed from trocar 2.

Figure 3H:
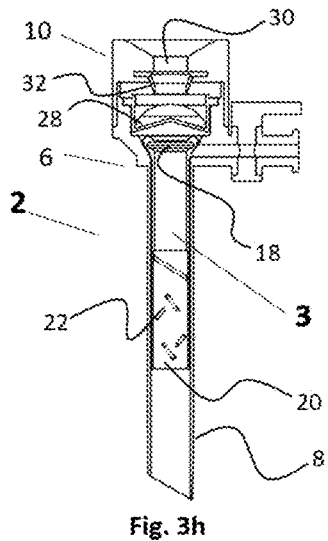

FIG. 3h is a cut view of trocar 2 containing the installed port adaptor 3 in cannula 8. The proximal opening 18 of port adaptor is installed under distal valve 28 of trocar 2. Cleaning cords 22 of port adaptor are shown.

Figure 3I:
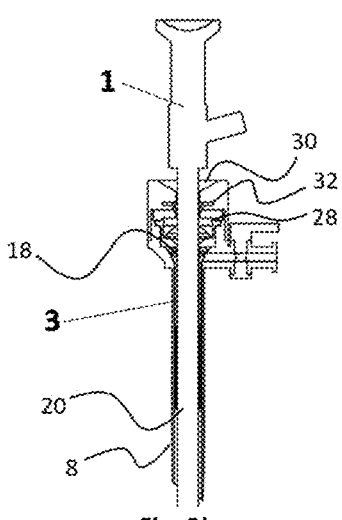

FIG. 3i is a cut view of endoscope 1 passing through trocar 2 that contains installed port adaptor cannula 8.

Figure 3J:
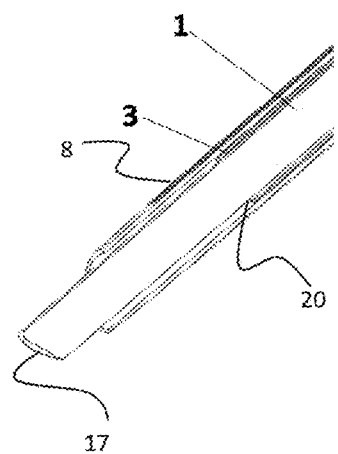

FIG. 3j is another cut view showing in detail the distal end endoscope 1 passing through port adaptor surrounds by cannula 8 of trocar 2.

FIGS. 4a-k illustrates another embodiment of the present invention where the endoscope lens port adaptor 4 is installed on the trocar 2 cannula.

FIG. 4a-d illustrate the structure of port adaptor 4. Port adaptor 4 is a thin-walled cannula having proximal opening 34 and distal opening 36. Port adaptor 4 has part of rough surface 38. Rough surface 38 increases the friction between port adaptor 4 and the patient body, eliminating port adaptor 4 to move from its insertion point 60, shown in FIG. 4h. The front end 40 of port adaptor 4 is sloping to facilitate insertion into the body. Cleaning cords 46 pass through holes 42 at the distal part of port adaptor 4. Round socket/recess 44 positioned around holes 42, below the surface of the cannula serve for keeping bulges 48 from standing out the cannula of port adaptor 4. The distal surface of port adaptor 4 may be covered with protecting sleeve having thin wall of 0.1-0.3 mm.

FIGS. 4e-k illustrate the process of installing port adaptor 4 on cannula 8 of trocar 2.

FIG. 4e illustrates obturator 50. An obturator is used to pierce and cut tissue for the purpose of inserting the trocar into the surgery site. Obturator 50 consist of shaft 52, handle 54 and sharpened distal end 56.

FIG. 4f demonstrates obturator 50 installed in port adaptor 4, with its sharpened distal end 56 extended from the distal opening of port adaptor 4. It should be noted that while obturator distal end 56 is inserted to port adaptor 4, its pointed head shifts cleaning cords 46 without tearing them.

FIG. 4g demonstrates port adaptor 4, positioned for example at the abdominal wall of the patient after the penetration.

FIG. 4h illustrates the removing of obturator 50 out of port adaptor 4.

FIG. 4i illustrates installing of trocar 2 cannula into port adaptor 4 cannula.

FIG. 4j demonstrates trocar 2 cannula installed in port adaptor 4 cannula.

FIG. 4k demonstrates endoscope 1 pass through trocar 2 and port adaptor 4.

FIGS. 5a-g illustrate another embodiment of the present invention where the endoscope lens port adaptor is inserted into trocar 2 cannula through the proximal opening of trocar 2.

FIGS. 5a-c illustrate the structure of port adaptor 5.

Port adaptor 5 comprises housing 64 and cannula 62. Housing 64 has proximal opening 66 and distal opening 68. Cannula 62 is attached to the distal opening of housing 64. Valve 72 is placed in the proximal opening 66 of housing 64. Hose connector 74 allows the surgeon to inject saline into port adaptor, when the surgeon wishes to rinse the inner surface of cannula 62 and cleaning cords 76. The surgeon also may use hose connector for attaching gas source to inflate the surgical site. Cleaning cords 76 located at the distal part of cannula 62. The cleaning cords pass through the thin wall of cannula 62 and have bulges 70 that keeps the cords in tension.

Figure 5D:
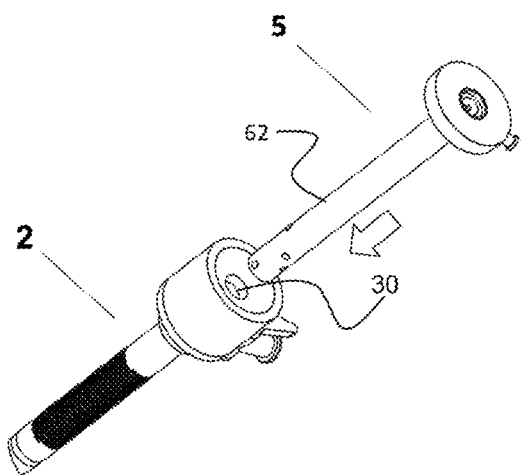
Figure 5E:
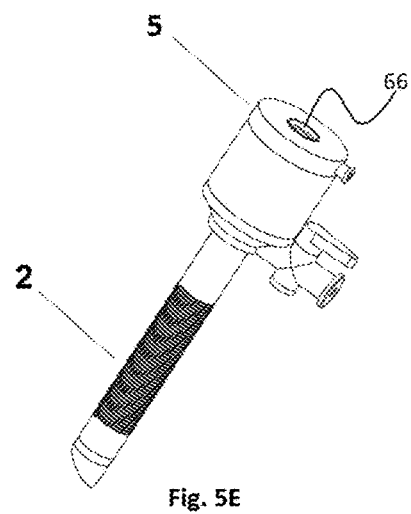

FIGS. 5d-e illustrate the installing process of port adaptor in trocar 2.

FIG. 5d illustrate the process of installing port adaptor 5 in trocar 2 by pushing cannula 62 of port adaptor through proximal opening 30 of trocar 2.

FIG. 5e demonstrates port adaptor 5 installed in trocar 2. Port adaptor 5 proximal opening 66 serve now as the opening for endoscope 1.

Figure 5F:
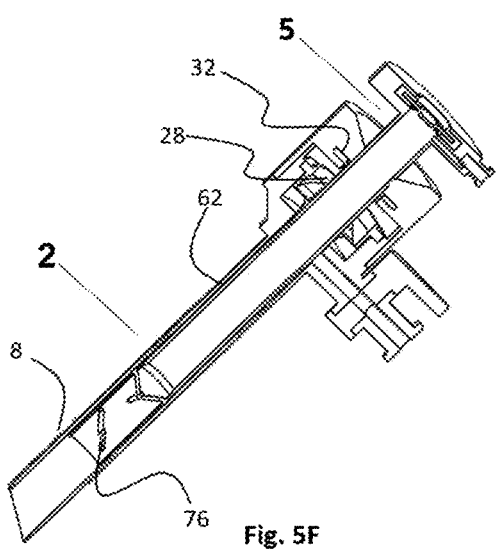

FIG. 5f is a cut view presenting port adaptor installed in trocar 2. In this figure, port adaptor 5 is not fully inserted for the purpose of clarity of the drawing. Cannula 62 of port adaptor 5 is shown here penetrating through valves 32 and 28 reaching the distal end of cannula 8 of trocar 2.

Figure 5G:
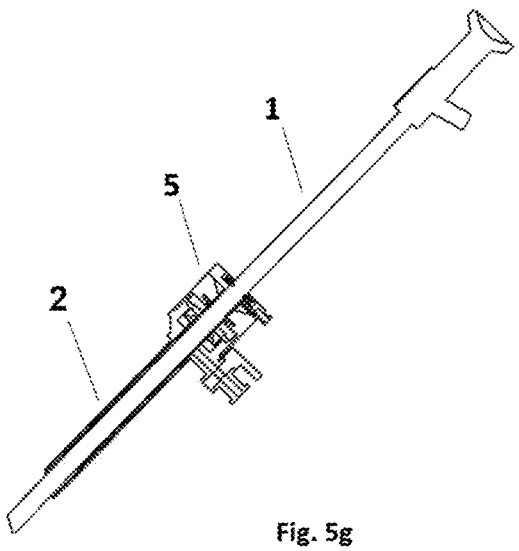

FIG. 5g is a cut view presenting endoscope passing through port adaptor 5 and trocar 2 to the surgical site.

As explained hereinabove in FIGS. 1a-k, a single elastic cord located in the center of a tube might enable wiping whole surface of the distal end of an endoscope, by pulling and pushing the endoscope distal end over the elastic cord while rolling the endoscope shaft, around its long axis, positioning the endoscope distal end in different angles with respect to elastic cord 23.

FIGS. 5h-i illustrate the structure of device 9. Device 9 comprises housing 63 attached to a cannula 61. Housing 63 includes proximal opening 57 and cannula 61 includes a distal neck 55 with opening 59. Cleaning cords 67 are positioned in cannula 61. Cleaning cords 67 pass through the thin wall of cannula 61 and have bulges 65 that keeps the cords under tension. Openings 69 located at the distal end of cannula 61 enable the surgeon to wash the endoscope lens using syringe 80, as is seen in FIG. 5J. FIG. 5j, shows an endoscope 1 passing through device 9 installed in the proximal opening of trocar 2. Syringe 80 is connected to trocar 2 through spigot 14, as seen in FIG. 5j. The role of distal neck 55 of cannula 61 is described in detail below with reference to FIG. 10d. While a single cord may be helpful to the surgeon, the process of pushing and pulling the endoscope over a single cord in various angles may be time and attention consuming, and not efficient enough for the surgeon To overcome this issue, an array of elastic cords may be much efficient, and will wipe the entire surface of the distal end of the endoscope with a single movement.

Figures 6A, 6B, 6C:
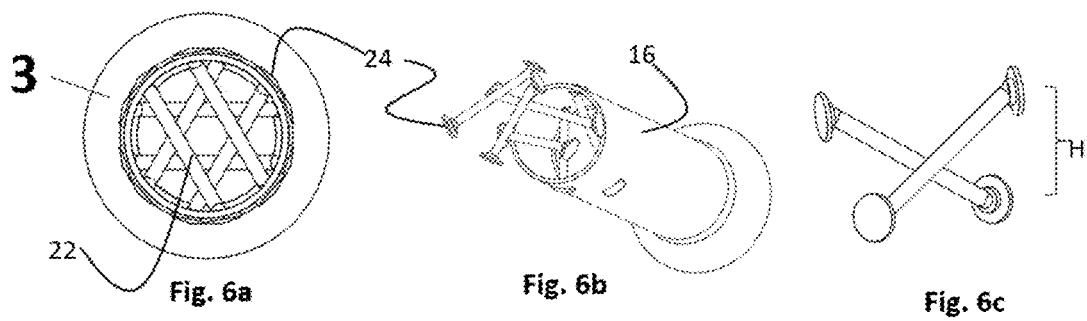
FIGS. 6a-6m illustrate various patterns, spatial arrangements, and cross-sectional shapes of cleaning cords that can be used with the present port adaptor.
Figures 6D, 6E:
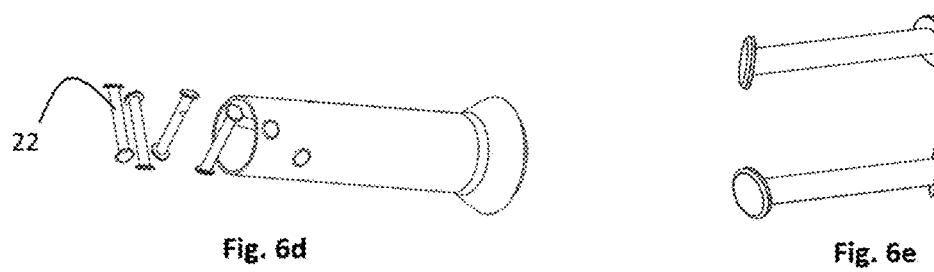

FIGS. 6a-e demonstrate first possible cleaning cords patterns and spatial arrangement and possible shapes of cleaning cords. FIG. 6f-j demonstrate another possible cleaning cords patterns and spatial arrangement. FIG. 6k-m demonstrate possible profiles of cleaning cords.

Figures 6F, 6G, 6H:
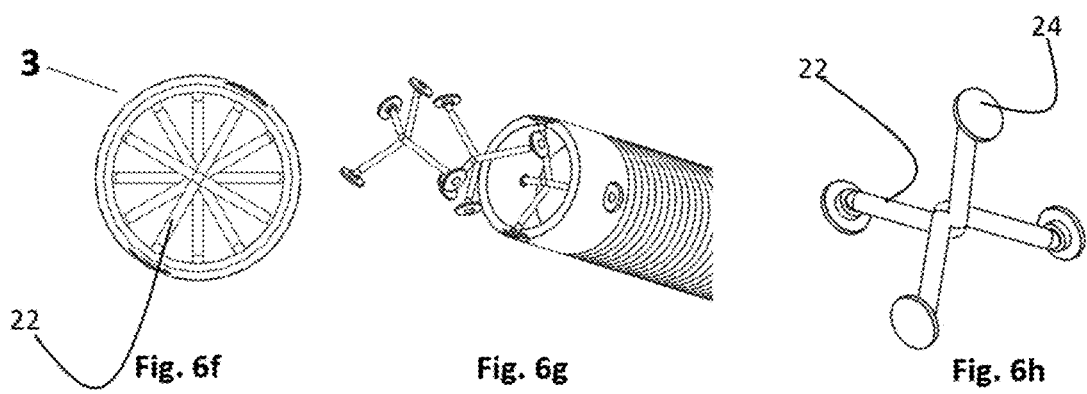

FIG. 6f illustrate mesh cords arrangement pattern where all cords around the center of the cannula.

The pattern shown in FIG. 6a includes 3 pairs of elastic cleaning cord, each pair located in different level in the tube as shown in FIG. 6b, with an offset of 120 degrees from each other. Each pair of elastic cords may include elastic cords angled in different directions with respect to each other as is shown in FIG. 6c, or arranged parallel to each other as is shown in FIGS. 6d-e.

Figures 6I, 6J:
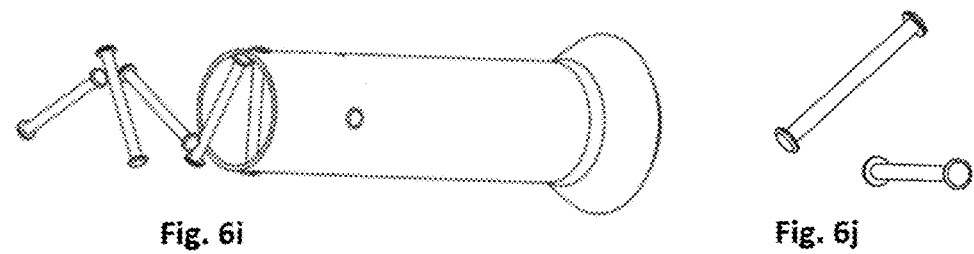
Figure 6K:
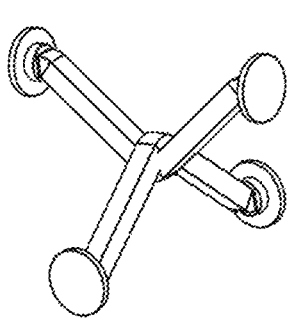
Figure 6L:
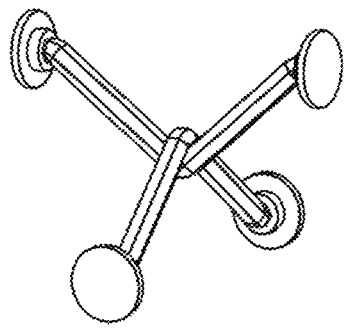
Figure 6M:
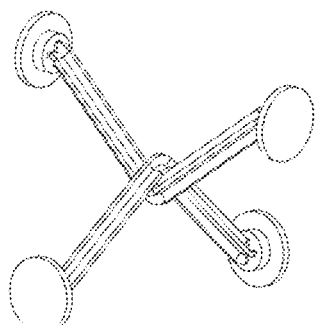

FIG. 6f illustrate concentric cords arrangement pattern where all cords pass through the center of the cannula. The pattern may include pairs of intersecting cleaning cords as is shown in FIGS. 6g-h. Alternatively, the cords can run in parallel planes to each other at different heights as is shown in FIGS. 6i-j.

It should be mentioned that the above patterns were tested and were very efficient in cleaning the endoscope lens and light source within a few seconds.

The elastic cord profile types may be round or have any other desired shape as shown in FIGS. 6k-m. FIG. 6k demonstrates rectangle profile while FIG. 6L demonstrates hexagon profile shape, and FIG. 6m demonstrates profile with cross shape.

The elastic cord material and dimensions may vary according to the tube diameter the endoscope diameter, and the kind of the surgical procedure.

When using port adaptor 3 in the trocar 2 cannula, the surgeon, during the surgical procedure, may wish to retrieve port adaptor out of cannula 8 of trocar 2. A tool having the shape of simple forceps, was designed to enable the surgeon to retrieve port adaptor out of trocar 2 cannula 8 in few seconds.

FIG. 7a presents retrieving tool 66. Tool 66 consists of handle 72 and two legs 68. Bulges 70 are located at the distal ends of legs 68. Legs 68 are flexible and may bent easily by the surgeon finger pressure.

FIGS. 7b-d show the way of using retrieving tool 66. In FIG. 7b proximal cap 10 of trocar 2 is removed and port adaptor 3 (not shown) is installed in trocar 2 cannula 8, under distal valve 28. To retrieve port adaptor 3, the surgeon pushes device 66 in the direction of arrow 76 into valve 28, while pressing legs 70 in the directions of arrows 74, as shown in FIG. 7b. FIG. 7c demonstrate tool 66 moving inside the cannula 8 of trocar 2 and the cannula of port adaptor 3 (port adaptor still not seen). FIG. 7d shows port adaptor 3 pulled out by device 66 in the direction of arrow 78.

FIGS. 7e-g are cut-away views of port adaptor 3 and device 66, illustrating the mechanism that enables the surgeon to retrieve port adaptor 3 out of the cannula 8 of trocar 2 without the need to spend time for accurate positioning device 66 with relation to port adaptor.

FIG. 7e demonstrates tool 66 positioned at the opening 26 of port adaptor 3. Opening 26 had inclined shape 29, that receives the inclined surfaces 71 of bulges 70. While the surgeon push device 66 forward the contact force between inclinations 29 and 71 force legs 68 to bent inside allowing legs 68 to slip inside the cannula of port adaptor 3.

FIG. 7f. demonstrates legs 68 of device 66 inside the cannula of port adaptor.

FIG. 7g. demonstrates bulges 70 locked in grove 25 that surrounds opening 26.

When tool 66 is locked to port adaptor, as shown in FIG. 7g, the surgeon simply continues to pull port 3 adaptor out of trocar 2.

FIGS. 8a-k illustrates a device for cleaning the inside surface of cannula 8 of trocar 2 and the inner surface of various configurations of the present port adaptor.

FIGS. 8a-b demonstrate the present practice for cleaning cannula 8 of trocar 2. While preforming minimal invasive procedure, when the surgeon needs to clean the inner surface of the cannula 8 or tries to wash the lens of the endoscope, the surgeon connects syringe with saline 84 to spigot 14 and injects the saline into the trocar. The injected saline then runs through cannula 8 over shaft 11 of endoscope 1 as is shown in FIG. 8b. This described practice is not very efficient since most of the saline runs on the lower surface of cannula 8 and the lower surface of the shaft of endoscope 1. Also, some saline remains in cap 12 of trocar 2 in area 86 (indicated by W). In addition, some of the saline runs slowly to the distal end of the endoscope and stays on the endoscope lens due to surface tension of the saline, which causes continuous distortion of the image as is described in detail with respect FIGS. 9a-e. To overcome this problem, the surgeon usually shakes the endoscope which may clear the lens momentary but causing the saline that remained in at cap 12 at area 86, to run on the endoscope shaft to the distal end of endoscope 1 shaft and repeat the continuous distortion of the image problem.

To solve the problem, the inventors developed simple and efficient device that creates high power saline jets that efficiently clean the inner surface of the cannula 8 of trocar 2, and the cannula of port adaptor 3 or the cannula of port adaptor 4 when one of them is installed, while eliminating the saline from staying on the endoscope lens. Also, the device is designed to inject the saline directly to opening of the cannulas eliminating the saline from staying in cup 12 of trocar.

FIGS. 8c-e demonstrate device 90. Device 90 has proximal housing 92 with cover 94. Cover 94 has proximal opening 102. Valve 104 is placed in housing 92 covering the distal end of opening 102. Hose 96 extends out of housing 92. Distal cannula 98 arises from housing 92.

The distal opening 100 of cannula 98 is narrowed to fit tightly the endoscope shaft.

Grooves 106 are placed around opening 100. The elongated shape of grooves 106 is designed to build pressure that will create saline jets around the endoscope shaft.

Figure 8F:
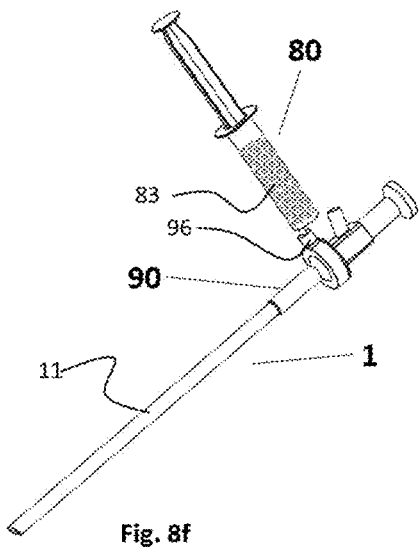
Figure 8G:
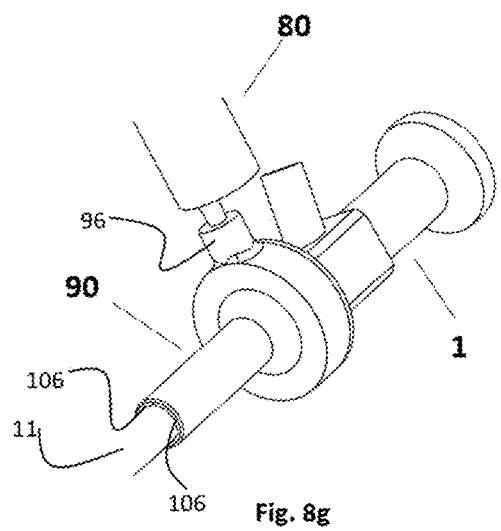

FIGS. 8f-g demonstrate device 90 assembled on endoscope shaft 11 while syringe 80 full of saline 83 is connected to device 90 through hose 96. Grooves 106 are shown arranged around shaft 11 of endoscope, where the endoscope shaft 11 serves as an inner wall, creating injection nuzzles around the endoscope shaft.

Figure 8H:
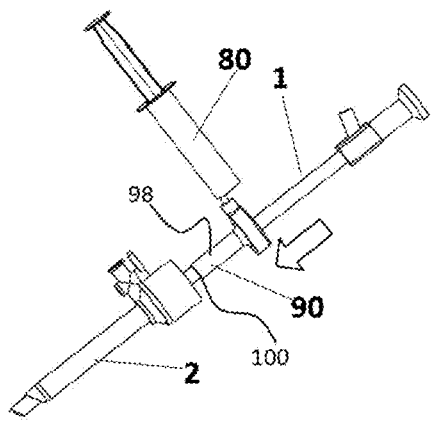
Figure 8I:
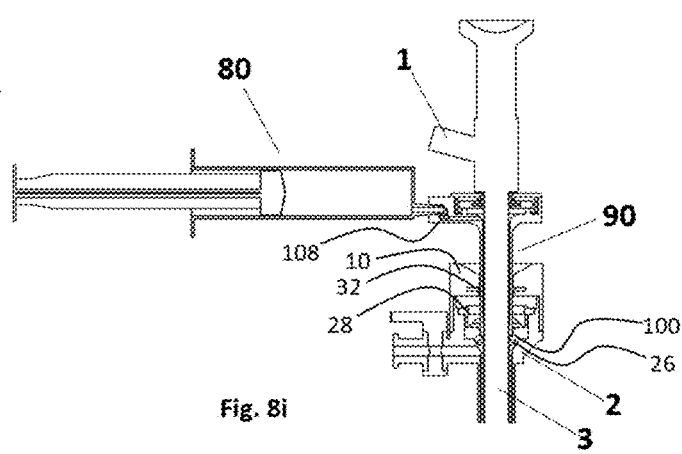

FIGS. 8h-i demonstrate use of device 90 to wash the inner surface of cannula 8 of trocar 2 and optionally attached port adaptors 3 and 4.

As is shown in FIG. 8h, the user slides forward the assembled device 90 over the endoscope 1 shaft 11. The diameter of shaft 98 is designed to pass through the opening of cap 10 and through both valves 28 and 32 of trocar 2. When distal opening 100 contacts the crown 26 of port adaptor as shown in FIG. 8i, the surgeon may inject the saline from syringe 80 to the housing of device 90. Since the distal opening of device 90 is in contact with the proximal opening of port adaptor 3, the saline flow directly to the cannula and does not leave any residuals in housing 12 of trocar 2. When the injected saline runs through elongated grooves 106, pressure is built, and jets of saline runs along the shaft of the endoscope without leaving any remains on the endoscope lens.

Figure 8J:
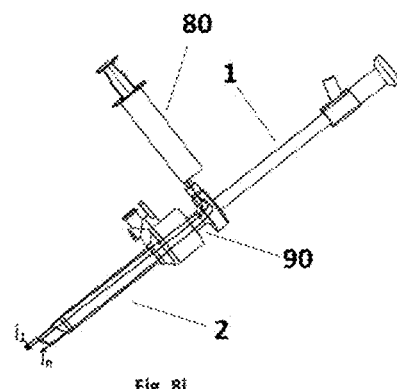
Figure 8K:
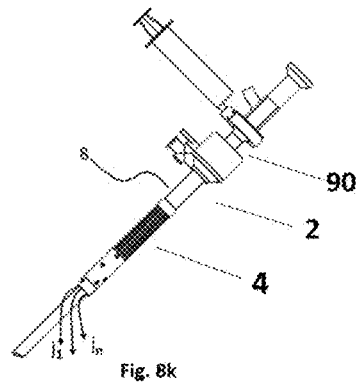

FIGS. 8j-k demonstrate the flow of the saline jets produced by device 90. FIG. 8j demonstrate the jets produced when no device is installed in trocar 2, or when port adaptor 4 is installed around cannula 8 of trocar 2 as is shown in FIG. 8k.

A surgeon using the cleaning devices described herein typically employs a syringe filled with liquid to wash the endoscope lens and the inner surface of trocar 2.

Accumulation of liquid in the trocar cannula can lead to liquid droplet formation on the endoscope lens even when the endoscope lens is completely clean. To solve this problem, the present inventors devised a trocar having a cannula with a contoured cutout on the distal end.

FIGS. 9a-e are photos of an experiment showing the phenomenon of liquid droplet accumulation and resultant image distortion even when the lenses of the endoscope are completely clean.

FIGS. 9*f-n* illustrate a novel design for a distal opening of a trocar that prevents the accumulation of liquid droplets on the endoscope lens.

Figure 9A:
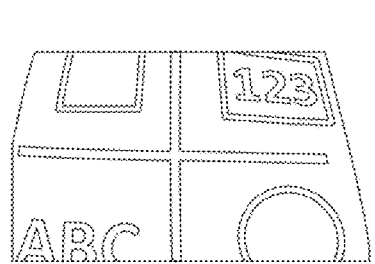
FIGS. 9a-9n illustrate photos (FIGS. 9a-9h) and illustrations (FIGS. 9i-9n) of liquid accumulation (FIG. 9a-e) in an endoscope positioned through a standard trocar (FIG. 9f) and a prototype trocar (FIG. 9g) constructed in accordance with the teachings of the present invention. The prototype trocar included a contoured cutout (FIGS. 9g, 9i-n) that facilitated draining of cleaning fluid from the trocar cannula and as a result prevented liquid droplet formation on the endoscope lens. In a standard trocar (FIG. 9f), liquid can be trapped in the cannula (FIG. 9b) leading to endoscope lens fogging and a distorted image of the surgical site.
Figure 9B:
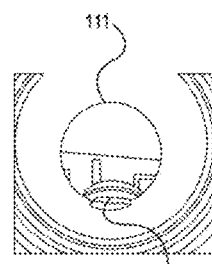
Figure 9C:
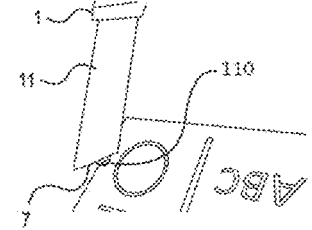
Figure 9D:
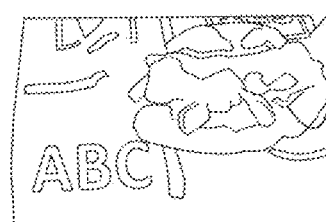
Figure 9E:
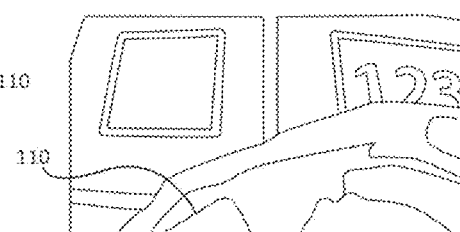
Figure 9F:
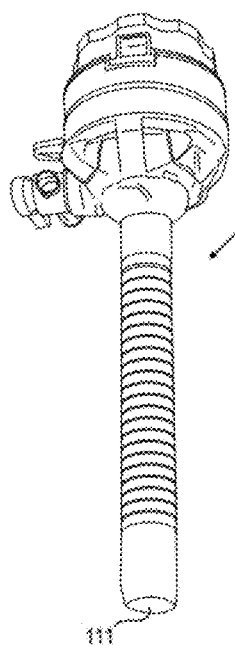
Figure 9G:
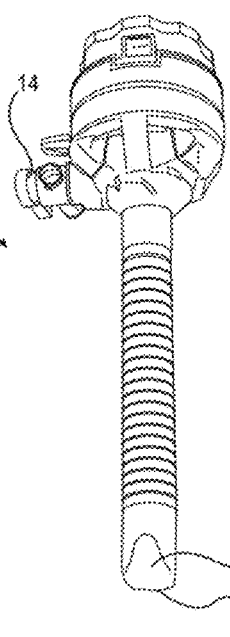

FIG. 9*a* is a scaling surface used for demonstrating the image quality captured by lens 7 of endoscope 1. While using cleaning liquid injected by syringe through spigot 14 shown in FIG. 9*g*, some drops 110 may stay at opening 111 at the distal end of cannula 8 of trocar 2, as shown in FIG. 9*b* and some other drops 110 may stay on the endoscope lens 17 as shown in FIG. 9*c*, causing image distortion as shown FIGS. 9*d-e*. Although the size of the drops is small compared to the size of lens 17 of endoscope 1, the image distortion may force the surgeon to stop the procedure until the drops are removed from lens 17. The present inventors noticed that due to surface tension phenomena, the drops 110 located at the distal opening of the trocar, shown in FIG. 9*b*, may pass to endoscope lens while the surgeon pushes and pulls the endoscope in and out of the trocar distal opening, causing re-building of drops on the endoscope lens. The inventors of the present innovation found that minor change of the common contour 111 of trocar opening shown in FIG. 9*f*, to contour 114 as shown in FIG. 9*g*, may reduce to minimum the amount of liquid that remains at the distal end of a trocar, after injecting liquid to the inner surface of a trocar, thereby eliminating drops from re-building on the endoscope lens.

FIGS. 9*i-n* illustrate cleaning devices (e.g., trocars with a removable cleaning depot) having a distal opening having the shape of contour 114.

Figure 9H:
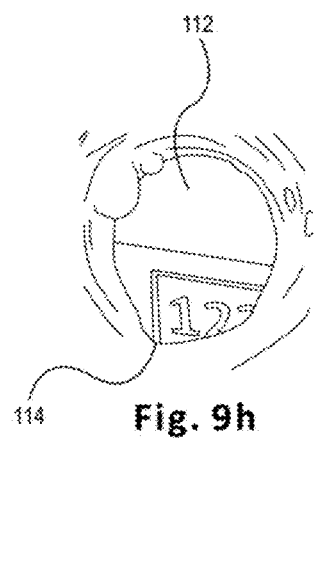
Figure 9I:
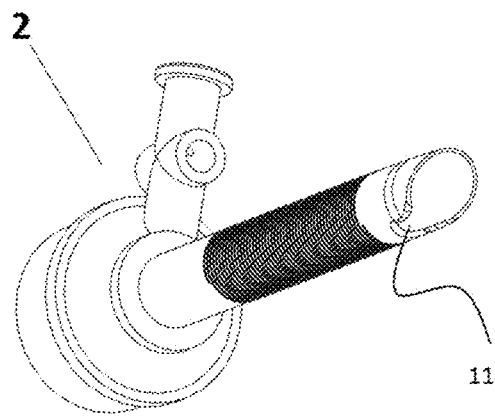

FIG. 9*i* illustrates a trocar with distal opening having the shape of contour 114.

Figure 9J:
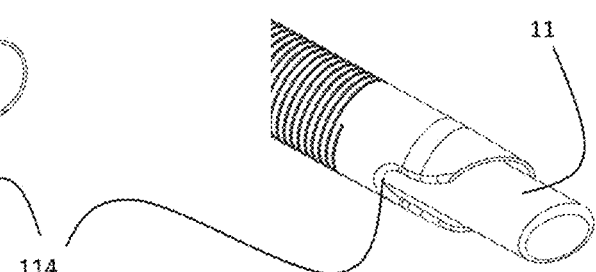

FIG. 9*j* illustrates the trocar of FIG. 9*i* with shaft 11 of endoscope 1 passing through the trocar opening.

FIG. 9*k* illustrates an elongated port adaptor 3 (cannula) with its distal end having the shape of contour 114.

FIG. 9*l* illustrates port adaptor 3 (described hereinabove) installed in the cannula 8 of trocar 2, with its distal end having contour 114 coming out of the distal opening of the cannula 8 of trocar 2. Contour 114 enables the liquid to drain out through contour 114 of port adaptor 3 and the cannula of trocar 2.

FIG. 9*m* illustrates device 4 with its distal end having contour 114.

FIG. 9*n* illustrates device 4 with its distal end having contour 114, installed on trocar 2 cannula 8, while shaft 11 of endoscope 1 comes out of the distal end of device 4.

The present inventors investigated the phenomena of liquid accumulation on the endoscope lens and found also that when an endoscope is advanced or retracted within a delivery cannula 8 of trocar 2, the endoscope shaft contacts the inner surface of the cannula. As a result, when the endoscope shaft is pulled out of the cannula it collects liquid present in the cannula that can fog the endoscope lens and distort the image presents to the surgeon on the screen.

The inventors of the present invention found that a small centering tube inserted into the opening of the trocar cannula may prevent the endoscope lens from passing through the drops of liquid accumulated at the distal opening of the trocar cannula.

FIGS. 10*a-d* illustrate endoscope centering devices used for preventing liquid accumulation on the endoscope lens.

Figure 10A:
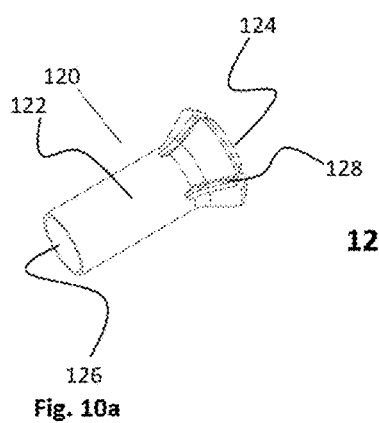
FIGS. 10a-10d illustrate several configurations of an endoscope centering device used for preventing liquid accumulation on the endoscope lens.

FIG. 10*a* illustrates a centering tube 120 having a length of about 20-30 mm with an external diameter that fits tightly the inner diameter of the trocar 2 cannula 8, and inner diameter of no more than +0.2 mm than the endoscope shaft diameter.

Device 120 is conical in shape opening 124 in order to prevent device 120 from completely passing through the trocar cannula. Slits 128 arranged around opening 124 allows cleaning liquid to run into and through device 120.

Figure 10B:
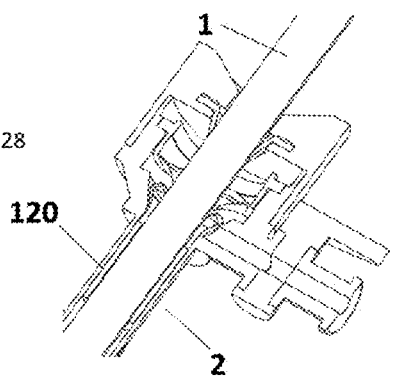

FIG. 10*b* is a cut-away view showing device 120 installed in the opening of the cannula of trocar 2.

Figure 10C:
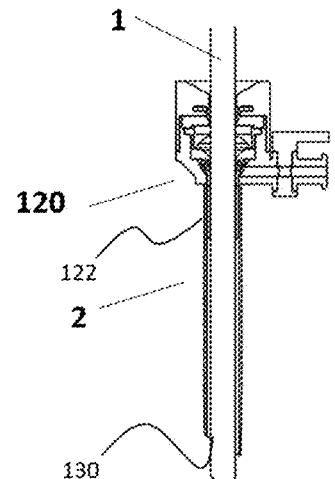

FIG. 10*c* is a cut-away view showing interval 130 between the shaft 11 of endoscope 1 and the inner diameter of the trocar 2 cannula 8. The size of interval 130 may be about 0.8 mm-0.9 mm in trocar size 11 and 1.3 mm-1.5 mm in trocar size 12.

Figure 10D:
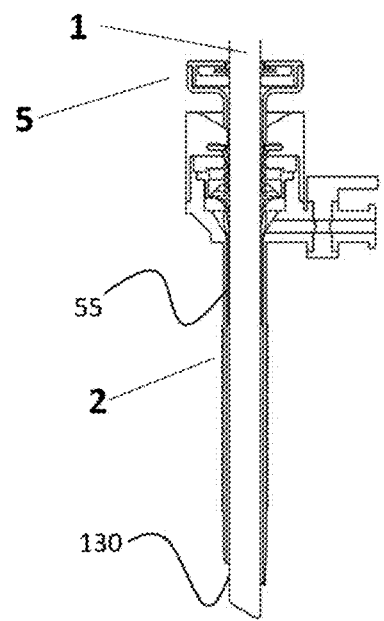

FIG. 10*d* is a cut-away view of device 9 with its centering neck 55 installed in the opening of cannula of trocar 2, showing tolerance 130 between the shaft of endoscope 1 shaft 11 and the inner diameter of the trocar 2 cannula 8.

Reference is hence made now to FIGS. 11 to 21. It is in the scope of the invention wherein a few embodiments of endoscope lens cleaning devices, each of which is configured to be installed in the trocar cannula, without a need to increase or use bigger size of the trocar for receiving the internal sleeve. As an example, if it is common to work with trocar size 11 for endoscope with 10 mm diameter, then there is no need to use trocar 12 for the sleeve. This is achieved by a design of the sleeve having a relatively big openings which configured to receive cleaning cords or, in another embodiment, were the distal opening of the cleaning head, protrudes out from the distal opening of the trocar, by the ability of the cleaning head, of this design, to expand, thereby allowing the endoscope to pass through the 3D positioned cleaning cords with a very small friction force. Also, the openings and the ability of the cleaning head to expand allows clotted blood and other fluids and particles to be cleansed, e.g., by being ejected out of the cleaning head, hence decreasing or otherwise eliminating re-contamination of the scope of the endoscope in the following cleaning.

Figure 11A:
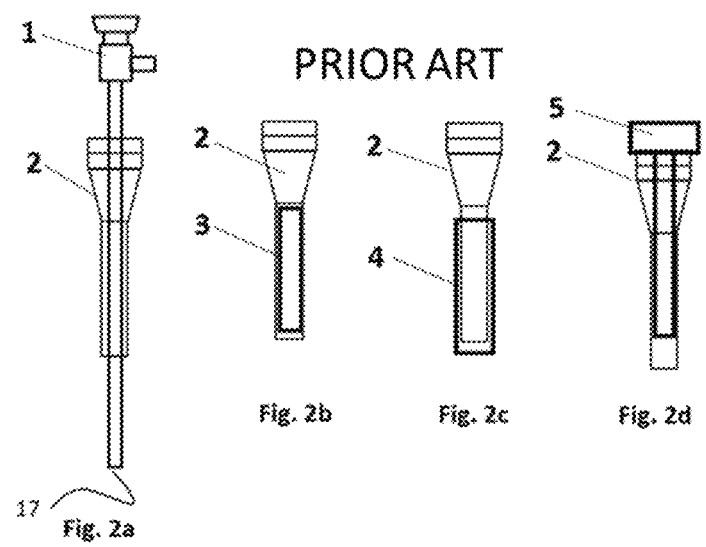

FIG. 11*a* schematically illustrates some possible embodiments of the endoscope lens cleaner device as was described in the prior art. FIG. 11*a* demonstrates three possible positions cleaning device, in the trocar cannula, around the distal opening of the trocar cannula, and placed through the proximal opening of the trocar where the distal end of the lens cleaner device is positioned in the trocar cannula.

Figure 11B:
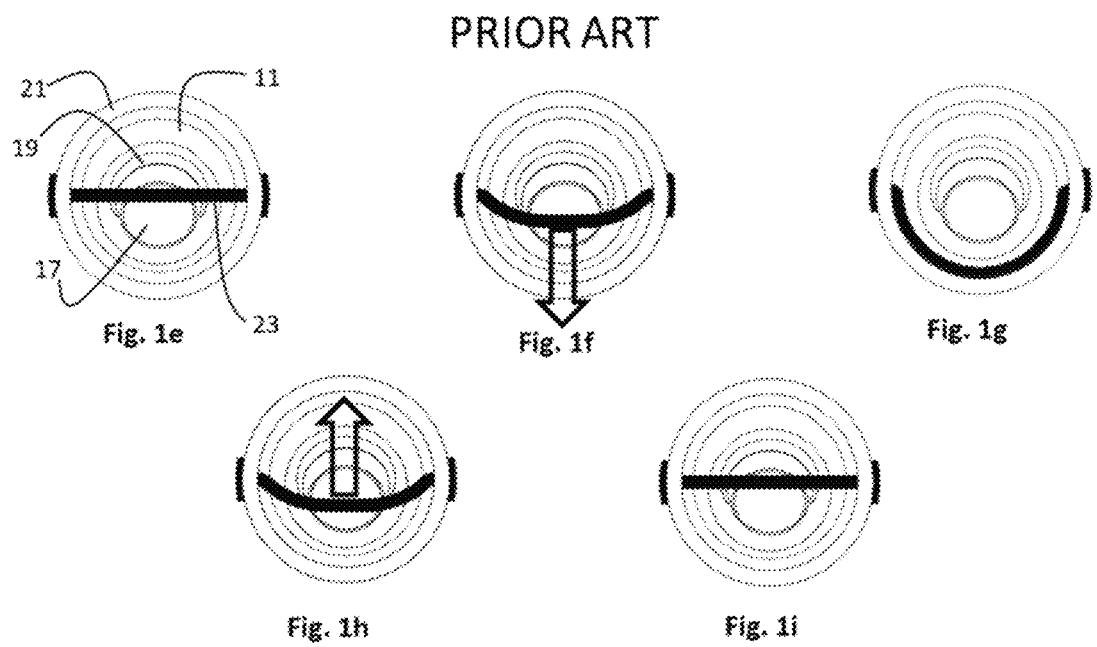

FIG. 11*b* illustrates schematically the use of single cleaning cord to wipe and clean the endoscope lens and light source, as was described in the prior art.

FIG. 11*c* illustrates one embodiment of the present invention where the endoscope lens cleaning device is installed in the trocar cannula.

FIG. 11*d* illustrates one embodiment of the present invention where the endoscope lens cleaning device is placed through the proximal opening of the trocar.

FIGS. 12*a-d* illustrate schematically some of possible install positions of the lens cleaning device according to the present inventions.

In FIG. 12*a*, lens cleaning device 3 is installed in trocar 1 cannula under duck valve 101 where the distal end of the device does not protrude from the cannula distal end.

In FIG. 12*b* lens cleaning device 5 is installed in trocar 1 cannula under duck valve 101 where the distal end of the device protrudes out from the cannula distal end.

FIG. 12*c* shows lens cleaning device 7 of the prior art which is installed through the proximal opening of trocar 1 cannula, where the distal end of device 7 does not protrude from the cannula distal end.

In FIG. 12*d* lens cleaning device 9 is installed through the proximal opening of trocar 1 cannula, where the distal end of device 9 protrudes out from the cannula distal end.

Reference is now made to FIG. 13*a*. Cleaning device 110 is installed in the trocar cannula as was described in FIG.

12a. Cleaning device 110 consists of a tube 130 and a proximal crown 150 that serves also as the proximal opening of tube 130. Tube 130 have distal opening 260.

Cleaning device 110 illustrated in FIG. 13a, is designed for cases where the cleaning device is installed in trocars having diameter that leave only small space between the inner diameter of cleaning device 110 and the outer diameter of the endoscope shaft, such as commercially available products by Covidien 11 or Ethicon 11, having typically inner diameter of about 11.5 mm that are commonly used for 10 mm diameter endoscope.

FIGS. 13a-d, further illustrate lens cleaning device 110. While the lens cleaning device 110 have very thin walls such as about 0.3 mm to about 0.4 mm, the inner diameter of lens cleaning device may be less the about 11 mm which leave very small space for the cleaning cords to slide around the shaft of about 10 mm endoscope while the endoscope travels along the cannula. In this case, the cords may apply excessive friction force on the endoscope, which may cause inconvenience friction to the surgeon that operates the endoscope, to jam the movement of the endoscope from moving or even or tear the cleaning cords.

To overcome this problem cleaning device 110, have large openings such as 340 and 180 shown in FIG. 13a. Cleaning cords 320, 300, and 200 are placed above openings 340, 180 and 230 respectively. When the endoscope slides over cleaning cords 320, 300, and 200 and push them aside, the side opening receives the cleaning cords allowing the cord to be stretched out of the inner surface of cleaning device 110, as shown in FIGS. 13c-d and in FIG. 18b which is a photo of a working protype of cleaning device 110.

FIG. 13b is illustration of typical cleaning cord 190. Cleaning cord 190 have medial stretchable string 350 connected by splays 330 to heads 310 at each side. Splays 330 increase the resistance to cord cutting when the endoscope slides over the cords, applying dragging force on the cleaning cord.

FIG. 13c illustrates endoscope 170 having shaft 290 that pass through proximal crown 150 to distal opening 250 of tube 130 of cleaning device 110. Stretchable cleaning cords 320, 300 and 200 are pushed aside by endoscope shaft 290 and shown sticking out of openings 340, 180 and 230 respectively.

FIG. 13d is illustration of magnified median part of cleaning device 110, demonstrating the extra space available for the cleaning cords 320, 300 and 200 in openings 340, 180 and 235 respectively.

It should be noted that the length of cleaning device 110 may allow opening 250 and cleaning cord to arise out of the distal end of the cannula of trocar 1 as was described in FIG. 12b or with proximal cap such as cap 7, like the one described shown FIG. 12c.

FIGS. 14a-f illustrate another embodiment of the present invention where the endoscope lens cleaning device is installed through the trocar cannula as was described in FIG. 12d.

Figure 14A:
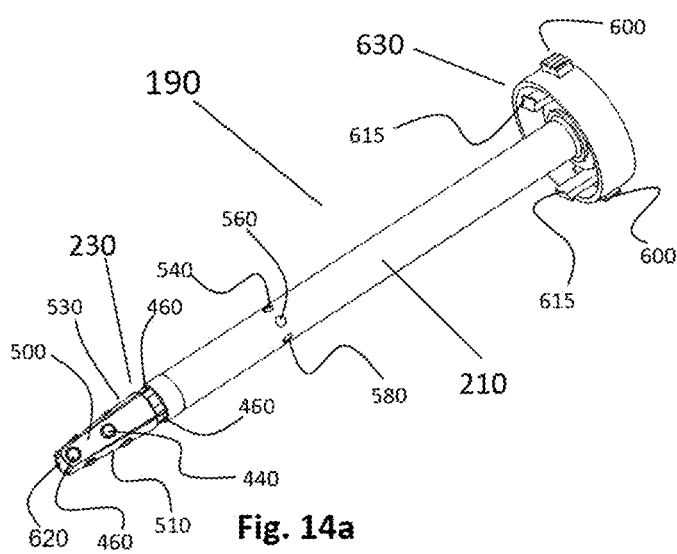
FIGS. 14a-14i illustrate another embodiment of the present invention where the endoscope lens cleaning device is installed through the trocar cannula.
Figure 14B:
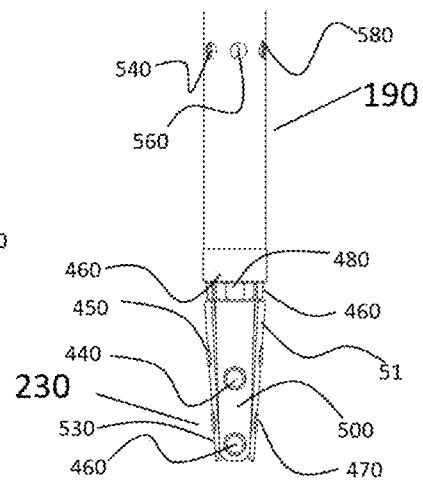

FIGS. 14a-b illustrate endoscope cleaning device 190 in details. Endoscope cleaning device 190 consists of median tube 210, proximal cap 630 and distal end cleaning mechanism 230. Median tube 210 have proximal end connected to proximal cap 630 and distal end connected to cleaning head mechanism 230. The median tube 210 has outer diameter which allows the insertion of cleaning device 190 into the cannula of trocar 1, through the proximal opening of trocar 1 as shown in FIGS. 14f-g. Holes 540, 560 and 580 located in median tube 210 are used for delivering gas for inflating the procedure site and for injecting saline into tube 210 for cleaning the distal cleaning head. Holes 540, 560 and 580 are designed to be located under the duck valve 101 (not shown here) of trocar 1, when the endoscope cleaning device 190 is installed in trocar 100. Cap 630 serves also as the proximal opening of cleaning device 190. Buttons 600 activate arms 530. Arms 615 are used to secure cleaning device 190 to trocar 100.

When the surgeon wishes to install cleaning device 190 in trocar 100, he pushes cleaning device 190 through trocar 100 proximal opening until arms 615 engage with the proximal cap of trocar 100. When arms 615 are locked into the proximal cap of trocar 100, cleaning head 230.

When the surgeon wishes to uninstall cleaning device 190 from trocar 100, he/she just presses buttons 600 and pulls cleaning device 190 out of trocar 100.

Figure 14C:
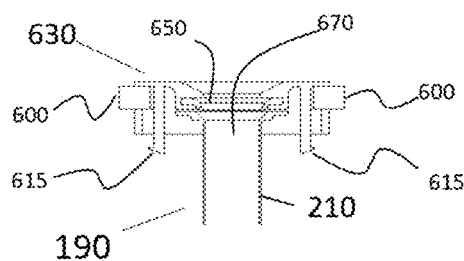

FIG. 14c is cut view of proximal end 630 of cleaning device 190. Median tube 210 have opening 670 connected to proximal cup 630. Seal 650 has round opening fitted to endoscope shaft, eliminating gas leaking when the endoscope is installed in cleaning device 190.

Push buttons 600 are connected to arms 615. Pressing both buttons move arms out of locking position and allows the surgeon to pull cleaning device 190 out of trocar 100.

The installing process and the disengagement of cleaning device 190 may be done in a second while the endoscope is installed in cleaning device 190. This enables the surgeon to keep the pace of the surgical procedure.

The distal cleaning mechanism 230 is located at the distal end of median tube 210. The cleaning head mechanism consists of flexible arms that may be bend in and out with respect to the long axis of median tube 210. Stretchable cords 400-430 are connected to the arms 500-530 forming spatial grid. When the surgeon wishes to clean the endoscope lens, he pulls the endoscope back to median tube distal opening just behind the distal cords and then pushes the endoscope back to the procedure site through the stretchable cleaning cords.

When the endoscope distal lens is pushed through the stretchable cords that form the spatial grid, the cords are forced tightly to the endoscope lens surface and slide in different directions over the lens to the side of the endoscope shaft. In the meantime, the distal end of the endoscope that moves through the cords grid, causes arms 500-530 to bent outside enabling the endoscope to move forward while increasing the initial length between the two ends of the stretchable cords causing the wiping force applied by the cleaning cords on the lens surface to increase.

FIGS. 14a-b and FIGS. 14d-e illustrate in detail the cleaning head 230 structure.

Cleaning head 230 inter alia consist of four arms 500-530. Slits separate between the arms. Arms 510-530 may be manufactured from metal or polymers. Each arm is connected to the distal opening by columns 460, creating hole 480 is between each pair of columns 460. The size of columns 460 is designed according to the material of the arms the amount of bending needed to enable the endoscope shaft to move through the arms while cords apply force on the endoscope lens.

In FIGS. 14a-b, the arms are in rest position and arms 500-530 are bent inward due to the tension applied by the cords on the arms. In the rest position the arms allow the surgeon to install or uninstall cleaning device 190 easily and safely since there is small or no friction force between the arms and cords heads 450-470 on the inner parts of trocar 100.

Figure 14D:
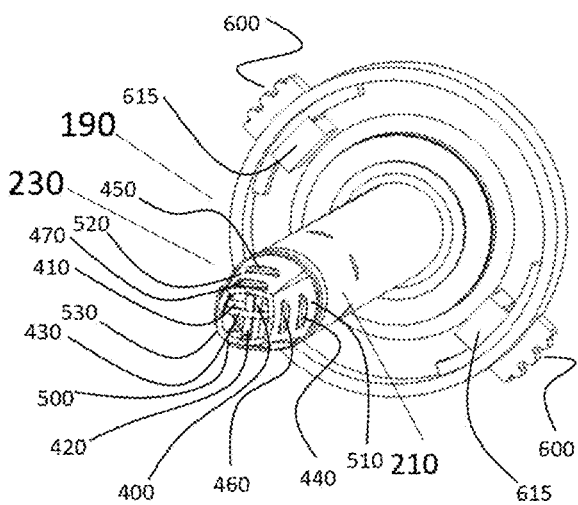

FIG. 14d is another view of cleaning head 230, exposing stretchable cords 400-430 structure in a rest position. Each cord is stretched between two opposed arms. Heads 440-470 holds each cord in the outer side of the arms. Arms 500-530 are bent inward and preform conical structure, due to the pretension force that the cords 400-430 apply on the arms. FIG. 14*d* illustrate spatial grid structure of cords where cords 420 and 430 are crossed where proximal cord 430 runs over distal cord 420, as be explained in more details in FIG. 14*e*.

Figure 14E:
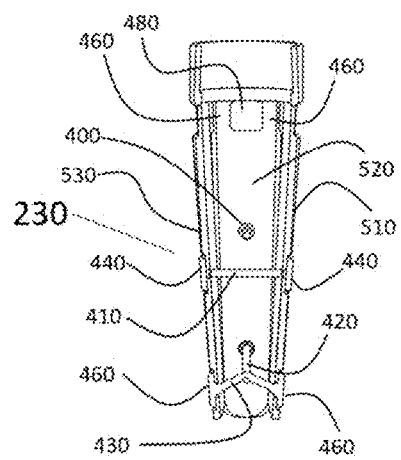
Figure 14F:
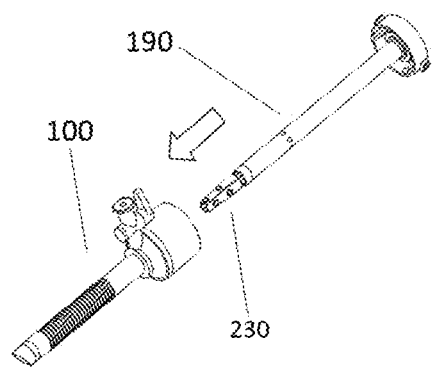
Figure 14G:
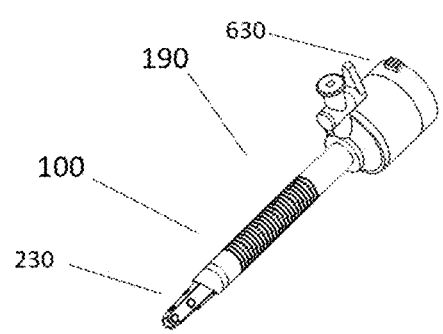

FIG. 14*e* is cross section of cleaning head 230, demonstrating the inner structure of the cords spatial grid. Cord 410 and cord 430 are installed on opposed arms 510 and 530. Heads 440 and 450 secure cord 410 and cord 430 to the arms. Cord 400 and cord 420 are connected to arm 520 and connected to arm 500, not shown in this section. While cords 400 and 410 are separated from each other, cords 420 and 430 are interconnected.

FIG. 14*f* illustrate the cleaning device 190 before installation in trocar 100. Cleaning head 230 of device 190 is pointed to the proximal opening of trocar 100 and surgeon moves device 190 toward trocar 100.

FIG. 14*g* illustrate the cleaning device 190 installed in trocar 100. Cleaning head 230 arises from the distal opening of trocar and proximal cup 630 is secured to trocar 100.

Figure 14H:
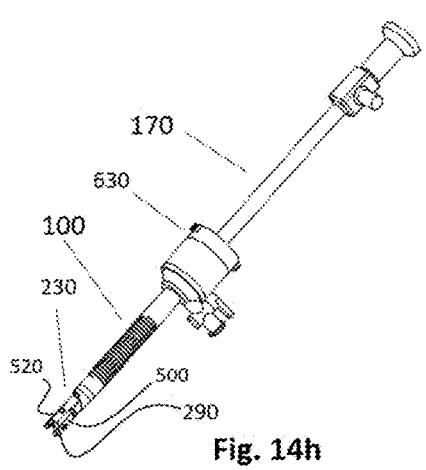

FIG. 14*h* illustrate endoscope 170 installed in cleaning device 190 while shaft 290 is moving inside cleaning head 230, causing arms 500-530 to bent outward.

Figure 14I:
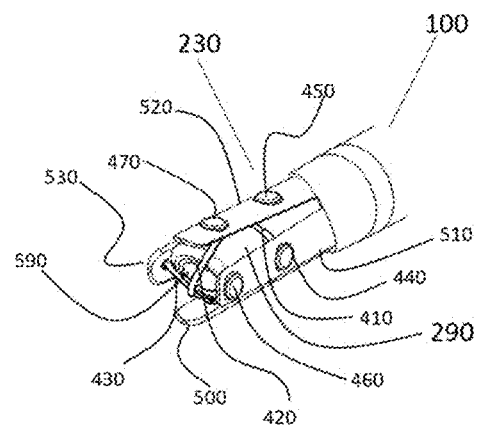

FIG. 14*i* is magnified illustrate of the distal end of shaft 190 of endoscope 170 while moving through cleaning head 230. While endoscope 170 shaft 290 is pushed against cords 400-430 of cleaning head 230 it causes arms 500-530 to bent outward, while cords 400 and 410 are pushed away to the side of the shaft 290, cleaning cords 420 and 430 are forced against lens 590, shown here preforming the lens wiping action where cord 420 wiping direction is to the side and wiping action of cord 430 is downward.

FIGS. 15*a-e* illustrate another embodiment of the present invention where the endoscope lens cleaning device is installed through the trocar cannula.

Figure 15A:
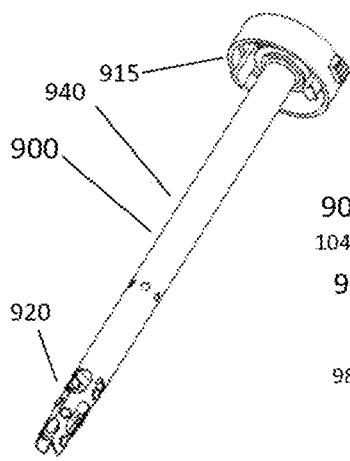
FIGS. 15a-15e illustrate another embodiment of the present invention where the endoscope lens cleaning device is installed through the trocar cannula.
Figure 15B:
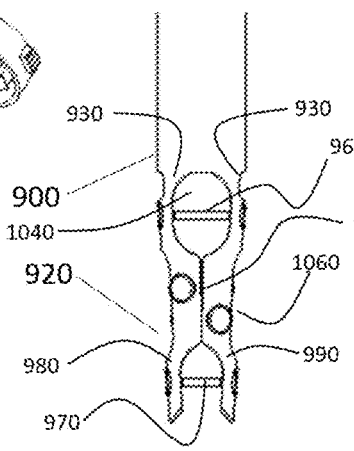
Figure 15C:
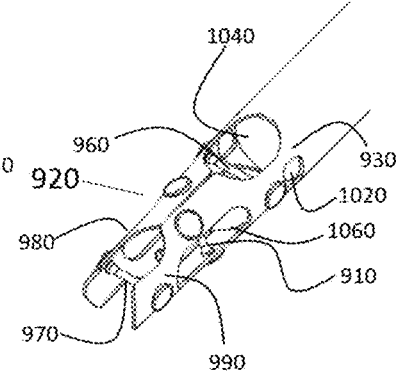

FIGS. 15*a-c* illustrate the structure of device 900 Cleaning device 900 consists of median tube 940 connecting proximal cup 915 and distal cleaning head 920. Distal head 920 consists of two arms separated by slit 1030 and opening 1040. Each arm contains openings 1020 and 1060. The structure of openings 1040 and 1020 create columns 930. Columns 930 allow arms 980 and 990 to bent inward when the endoscope shaft is not positioned in cleaning head 920, and outward while endoscope shaft travel through cleaning head 920. Openings 1040 and 1020 and 1060 serves also for draining blood and allow other material, wiped by the cleaning cords to fall out of cleaning head 920. Cleaning cord 960 located above the middle of opening 1040, and cord 970 located at the distal opening of cleaning head 920, connect arms 980 and 990 parallel to a center plane of cleaning head 920. While cords 940 are crossed and placed on rectangle plane to the plane of cords 980 and 990 located at the middle of opening 1060.

Figure 15D:
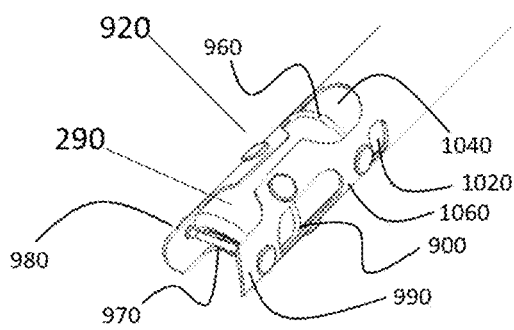

FIG. 15*d* illustrates distal end of shaft 290 of endoscope 170, while moving through cleaning head 920. In the instance illustrated in FIG. 5*d* the lens of the endoscope is approaching distal cord 970 while cords 940 and 960 were pushed to the side of shaft 290 into openings 1040 and 1060.

To allow the endoscope to pass through cleaning head 920 arms 980 and 990 are bent outward increasing the width of slit 1030.

Figure 15E:
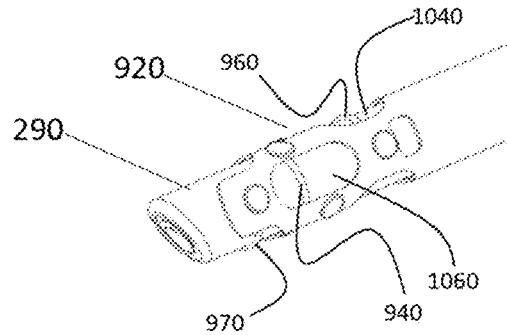

FIG. 15*e* illustrates distal end of shaft 290 of endoscope 170 arising out cleaning head 920. Distal cleaning cord 970 is pushed down around the endoscope shaft 270.

While the cleaning cords were pushed the side while wiping material from the surface of the endoscope lens, the wiped materials were ejected through the openings 1040, 1060 and the distal opening of cleaning head 920.

FIGS. 16*a-e* illustrate another embodiment of the present invention where the endoscope lens cleaning device is installed through the trocar cannula having small diameter.

Figure 16A:
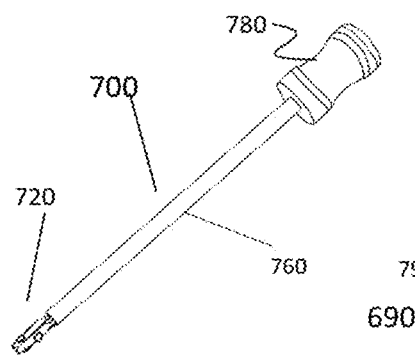
FIGS. 16a-16e illustrate another embodiment of the present invention where the endoscope lens cleaning device is installed through the trocar cannula having small diameter.

FIG. 16*a* illustrates cleaning device 700 consists of median tube 760 connected to proximal cup 780 and to distal cleaning head 720.

Figure 16B:
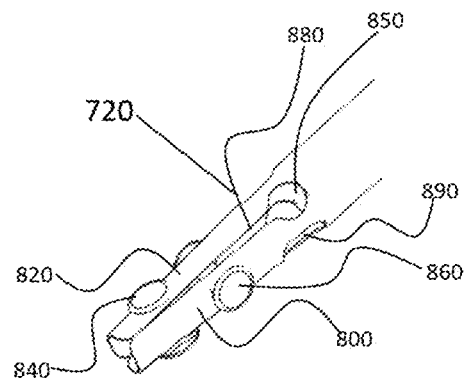

FIG. 16*b* illustrates distal cleaning head 720. Distal cleaning head 720 consists of 2 arms 800 and 820 separated by slit 880 and opening 850. Opening 860 and opening 880 create columns 870. Columns 870 allow arms 800 and arms 820 to bent inward and outward.

Figure 16C:

Reference is now made to FIGS. 16*a-e*. FIG. 16*a-c* illustrate device 700 installed in a 5-size trocar where proximal cup of cleaning device 700 is engaged with proximal cup of trocar 690. Cleaning head 720 arises from the distal end of trocar 690.

Figure 16D:
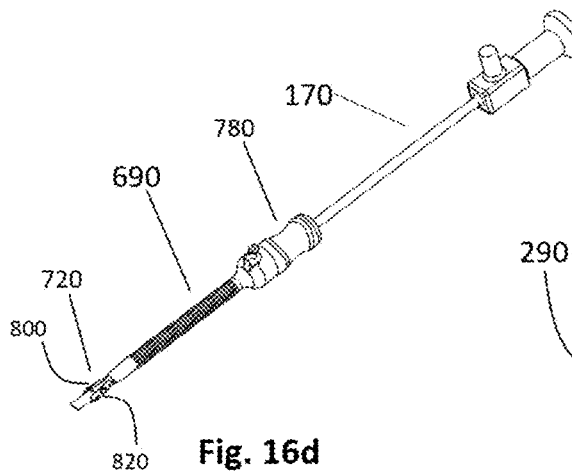
Figure 16E:
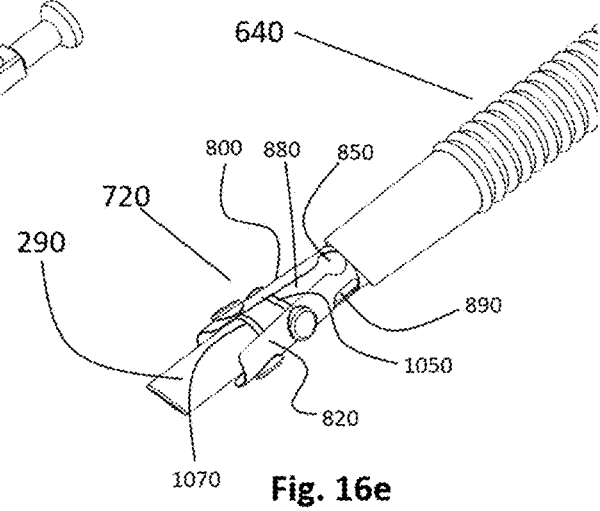

FIGS. 16*d-e* illustrate endoscope 170 installed in cleaning trocar 690. While passing through cleaning head 720 the endoscope causes arms 800 and 820 to bent outward. When arms 800 and 820 are bent outward slit 880 is enlarged and the materials wiped by cleaning cords 1050 and 1070 are ejected through slit 880 and opening 850 and 890.

FIGS. 17*a-c* illustrate another embodiment of the present invention where the endoscope lens cleaning device is installed in the trocar cannula as was described in FIG. 12*b*.

Device 740 have median tube 770 connected in its proximal opening to crown 150 and its distal end connected to cleaning head 230 that was described in FIGS. 4*a-i*. Crown 150 has conical shape that serves as stopping point, preventing device 740 to sleep completely into the cannula of trocar 100, and used also for receiving retrieving tool. Holes 730 in crown 150 enable gas and liquid to go through tube 770.

FIG. 17*b* schematically shows endoscope 170 when it passes through device 740 installed in trocar 100. Cleaning head 230 arises from the distal opening of trocar 100.

FIG. 17*c* is a cut view exploring device 740 (shows here by its details) installed in trocar 100 while shaft 290 of endoscope 170 passes through cleaning device 740. Crown 150 is located under valve 1010 allows gas and saline to pass from spigot 1090 of trocar 100 to pass into tube 770 of cleaning device 740 and to the cannula of trocar 100.

FIG. 18*a* is a photo of cleaning device 110 installed in the cannula of trocar 100 size 110 manufactured by Covidien, while shaft 290 of endoscope 170 pass through trocar 100 and cleaning device 110.

FIG. 18*b* is a photo of endoscope 170 passes through cleaning device 110 prototype. Cleaning cords 320, 300 and 200 are shown arising out of the openings in tube 130.

FIGS. 19*a-c* are photos of a prototype of device 210 of the invention, as described in FIGS. 4*a-i*.

FIG. 19*a* is a photo demonstrate cleaning head 230 with the arms in rest position, where the endoscope is not positioned in cleaning head 230 and the cords pull the arms radially and bent them inside. The resting state it is enables the surgeon to easily insert the device into the trocar or retrieve the device out of the trocar.

FIG. 19*b* is a photo demonstrate endoscope 170 distal end 290 positioned in cleaning head 230. In this state the arms are bent outward and the slits between the arms are enlarged, allowing blood and other wiped material to be ejected through the slits.

FIG. 19c is a photo demonstrate endoscope 170 distal end 290 positioned out and distally to the cleaning head 230. Cleaning cords 400, 420 and 430 may be seen through the slits.

FIGS. 20 a-c are photos of prototype of device 900, as described in FIGS. 5a-e.

Figure 20A:
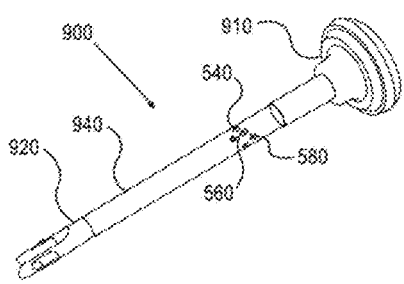
FIGS. 20a-20c are photos of another embodiment, as described in FIGS. 15a-e.

FIG. 20a is a photo demonstrate cleaning device 900.

Figure 20B:
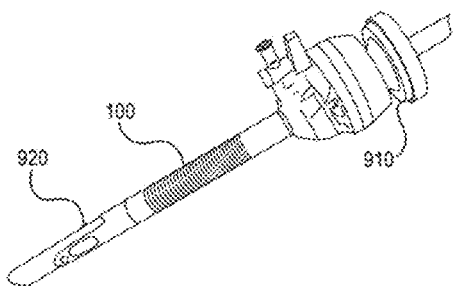

FIG. 20b is a photo demonstrate cleaning device 900 installed in Ethicon trocar size 11. Endoscope 170 is installed in cleaning device 900.

Figure 20C:
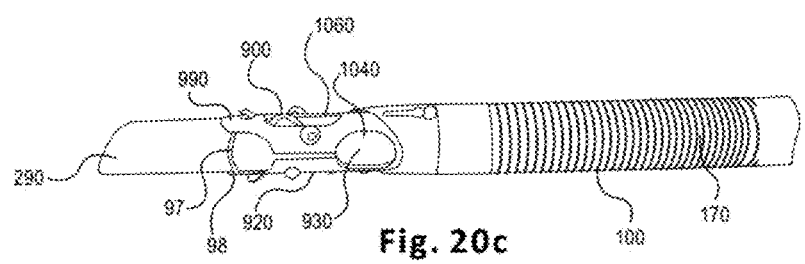

FIG. 20c is a photo demonstrate cleaning head 920 of device 900 installed in Ethicon trocar size 110. Endoscope 170 is installed in cleaning device 900 with its distal end 290 positioned out distally from the distal trocar opening. Cleaning cord 900, 930 and 970 may be seen arising from openings 1040, 1060 and the distal opening of cleaning device 920.

Figure 21A:
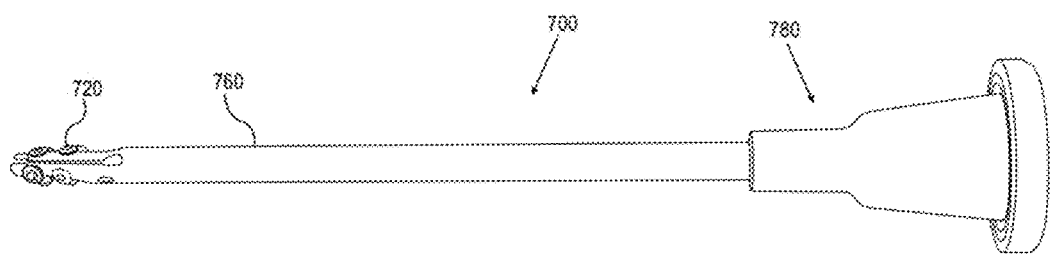
FIGS. 21a-21b are photos of another embodiment, as described in FIGS. 16a-c.
Figure 21B:
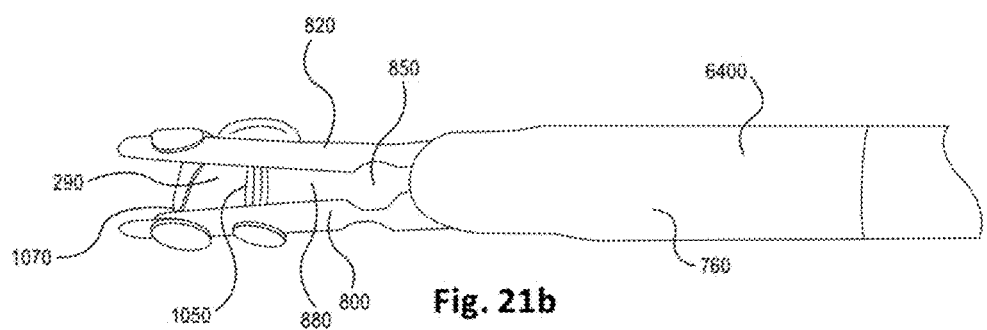

FIGS. 21a-b are photos of device 700 for commercially available Ethicon Xcel trocar size 5, as described in FIGS. 6a-c.

Additional objects, advantages, and novel features of the present invention will become apparent to one ordinarily skilled in the art upon examination of the following examples, which are not intended to be limiting.

FIG. 22-26 are photos of the experiment setup.

FIG. 27 presents Various bands' orientations and configurations.

FIG. 28 presents both endoscopes 30°-Degree lens and 0°-degree lens (distal end).

Figure 29:
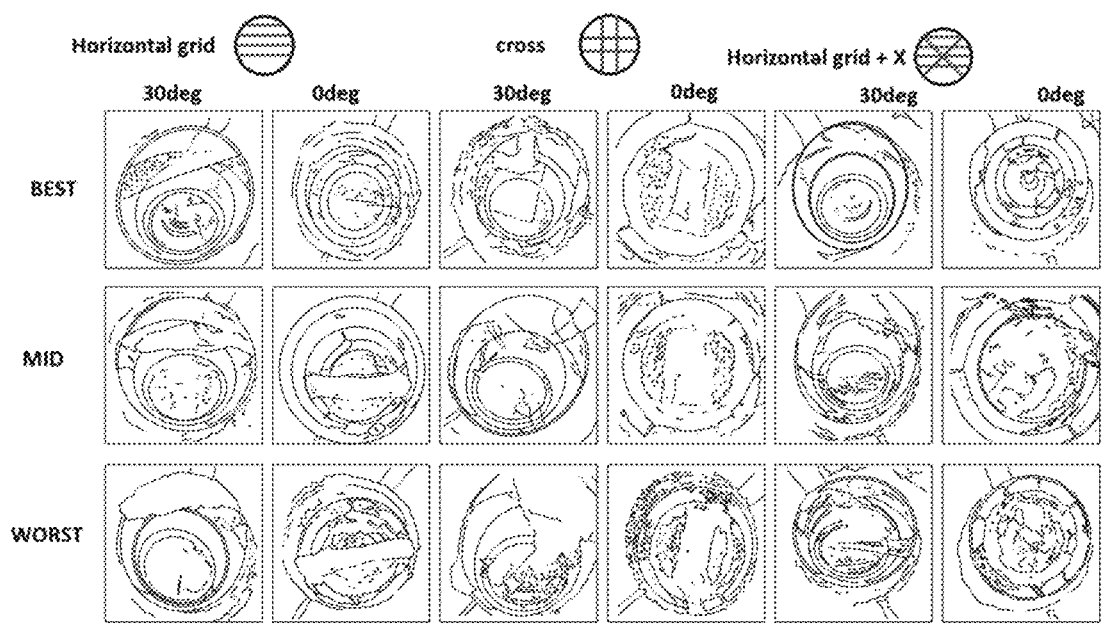
Figure 30:
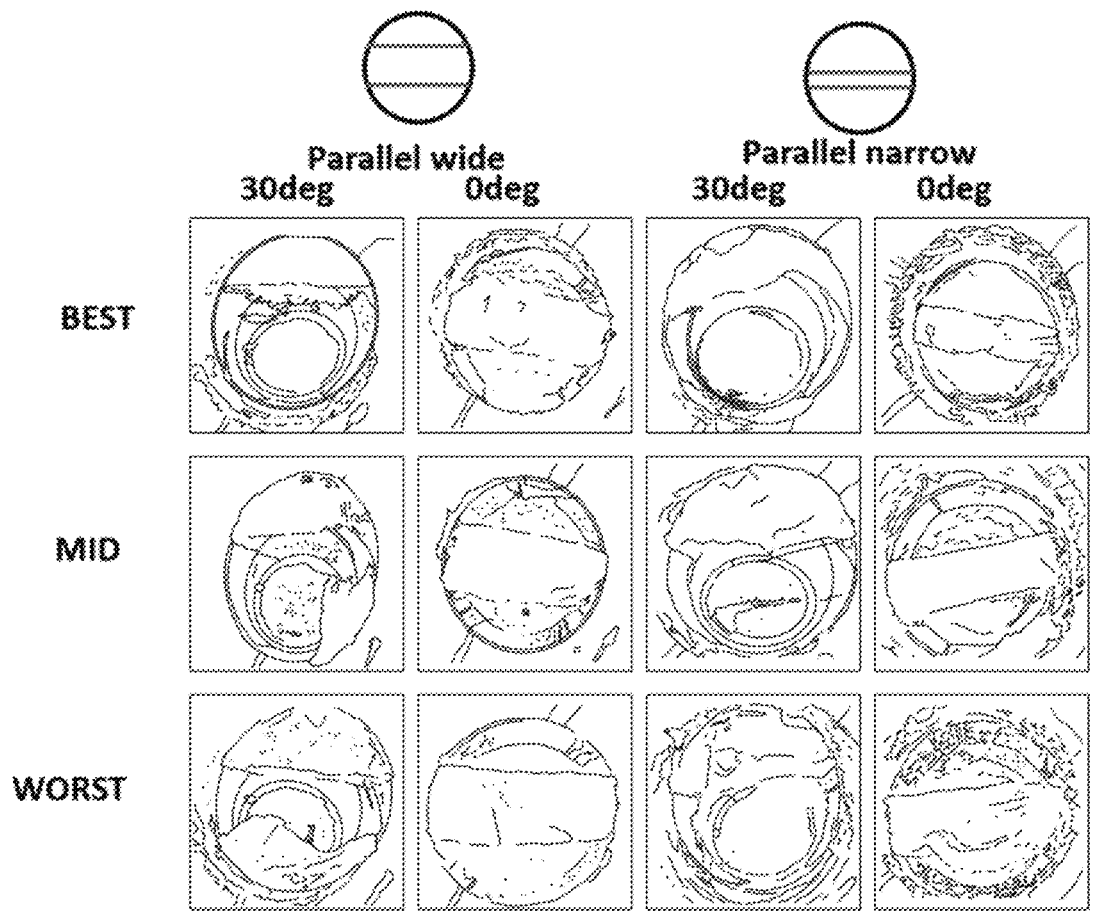

FIG. 28-30 present Wiping results by the various bands' orientations and configurations.

Example I

Reference is now made to the following example, which together with the above descriptions, illustrate the invention in a non-limiting fashion in FIG. 9.

Fabrication and Testing of a Prototype Port

A prototype of the present contoured trocar was fabricated by modifying the distal end of a Medtronic size 11 trocar (FIG. 9g); adapters (3 and 4) were manufactured via 3D printing. The prototype trocar and a Medtronic size 11 trocar (FIG. 9f) were tested for efficacy by injecting saline via valve 14 (FIGS. 9f and g) through both trocars.

The results showed significant difference between the volume of saline remaining in the distal end of the trocars as may be seen in FIG. 9h vs FIG. 9b. The volume of saline retained in the standard trocar was significantly higher than the volume retained in the trocar with contour 114. Since removing remaining saline from the distal end of a standard trocar takes time and effort, use of the present trocar (with contour 114) will not only lead to cleaner endoscope, but it will also reduce the time of procedure.

Example II

Reference is now made to the following example, which together with the above descriptions, illustrate the invention in a non-limiting fashion in FIGS. 22-30.

FIG. 22-26 are photos of the experiment setup. The experiment was set as follows: Endoscopic camera (5 mm, 0°-degree) was used to capture the cleaning action of the different patterns of cleaning strings. The camera was connected to one side of the adapter. Size 11 trocars, each have built in cleaning string pattern were connected to the other side of the adapter.

In order to capture and evaluate the cleaning process, an ointment was applied on the endoscope distal surface, then, the endoscope was inserted to the trocar and pushed forward to clean the ointment off the distal surface. The process was captured on video and saved. After each cleaning, the trocar was removed, and cleaning strings were washed and cleaned. The final result of each cleaning is shown in the following FIGS. 28-29, in order to allow a comparison between the performance of the different templates of the cleaning strings.

In order to compare the wiping results of the different concepts as described in Scopix patent (FIG. 8) of patent US20200060536A1, prototypes of the embodiment were produced. Each prototype of the embodiments was used to clean 0-degree and 30-Degree endoscopes. Before each cleaning, the tip of the endoscope was smeared with an opaque ointment uniformly, so that the lens and the light source were completely hidden. Before each cleaning, the cleaning device and the cleaning strings was cleaned. Each cleaning was captured by video. Each cleaning result was captured as picture. From each series of cleanings pictures, a picture of the best cleaning, a picture of the worst cleaning and a picture of a cleaning of medium quality was selected. All the final images were grouped together, as shown in the next slides.

Members 2201-2206 are denoted for screen, Endoscope 5 mm 0°-Deg, adapter, ointment, endoscope with ointment, and trocars with cleaning strings (bands), respectively. Various bands' orientations and configurations are presented in FIG. 27. Both endoscopes 30°-Degree lens and 0°-degree lens (distal end) are presented in FIG. 28. Wiping results by the various bands' orientations and configurations are presented in FIG. 28-30.

Results of the 30d-Deg scope cleaning

The Horizontal grid+x pattern cleaned effectively the 30-deg scope. The lens area is fully wiped, and the optic fiber is fully wiped too.

The Horizontal grid pattern may clean effectively the 30 deg scope: The lens area is fully wiped, while the optic fiber stayed partly covered.

The cross pattern cleans effectively the 30-deg scope: The lens area is fully wiped, but the optic fiber was still partly covered.

The parallel wide pattern does not clean effectively the 30-deg scope. In most of the cases lens area is not fully wiped. And the optic fiber was partly covered in most of the cases.

The parallel narrow pattern does clean effectively the 30-deg scope. In most of the cases lens area is fully wiped, but in most of the cases, the optic fiber maintained partly covered.

Results of the 0-deg scope cleaning:

The Horizontal grid+x pattern cleaned effectively the 0 deg scope. The lens area is fully wiped, and also the optic fiber was fully wiped.

The cross pattern does not clean effectively the 0 deg scope. Due to the pattern of the cleaning strings, the cleaning strings were not able to reach the area in front of the lens.

The parallel narrow pattern does not clean effectively the 0 deg scope. Due to the pattern of the cleaning strings, the cleaning strings were not able to reach the area in front of the lens.

The parallel wide pattern does not clean effectively the 0 deg scope. Due to the pattern of the cleaning strings, the cleaning strings were not able to reach the area in front of the lens.

The Horizontal grid pattern may clean effectively the 0 deg scope. In some cases, the cleaning strings wipe the area in front of the lens, leaving only thin horizontal area untouched.

Discussion of the Results:

The Horizontal grid+X pattern success in cleaning the camera surface in front of the lens area as well as the whole area of the optical fibers that provide the necessary illumination to obtain a quality image of the surgical area, stems from the three-dimensional arrangement of the cleaning strings along the trocar cannula, and the strings graduate horizontal different heights inside the trocar. This arrangement allows the strings, to slide down and overlap the previous cleaned areas of the endoscope lens as will be explained here.

When an endoscope is pushed distally in the cannula, it moves along the horizontal three-dimensional grid structure of the strings, some of the proximal strings may be positioned below the center of the endoscope lens and some above the center of the endoscope lens. The lower strings are forced to slide downward the endoscope lens when the endoscope push them, while the higher strings are forced to slide upward the endoscope lens when the endoscope push them.

When a distal string slides over the endoscope lens, it overlaps an area that was cleaned by the previous proximal cleaning strings, thereby increasing the chance of perfect cleaning.

While the horizontal strings pattern wipes most of the endoscope lens area, there may sometimes be a lack of overlap in the middle area leaving the middle part of the lens uncleaned. In this instance the strings in the X pattern located at the distal end of the cannula in a rectangle plane with respect to proximal horizontal strings, enabled final wiping of the whole surfaces of the 0-degree endoscope.

The parallel patterns and the cross pattern are flat (i.e., located on the same plane) allowing only one transition of each string over the 0 degrees endoscope surface. The strings movements are not over lapping, leaving large area in the center of the surface untouched, blocking the camera lens.

In this experiment two types of parallel pattern were tested: Wide configuration—4 mm distance between the strings; and narrow configuration—2.5 mm distance between the strings.

In the case of 0-degree endoscope, when the distance between strings is wider, a bigger part in the middle remains unwiped, while in the case of 30-degrees endoscope a bigger part of the endoscope surface is wiped.

In the case of 0-degree endoscope, when the distance between strings is narrower, a bigger part in the middle is wiped, while in the case of 30-degrees endoscope a bigger part of the endoscope surface is unwiped.

The cross pattern allows effective cleaning of 30 degrees camera, while the edge of the endoscope is forced to move through one of the intersections that are formed by the cross structure. During the passage, 2 strings are pushed simultaneously with an overlap between them, which causes an effective cleaning of the surface of the endoscope over which they pass. However, the front area of the endoscope that passed inside the intersection was not wiped by the strings and therefore a characteristic small triangle of uncleaned area can be seen. This area typically covers partly the optical fibers and may reduce their effective lighting area.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

The invention claimed is:

1. A port adaptor for a surgical port comprising
an adaptor body and
at least one elastomeric band stretched and reaching from one side of an internal lumen wall of said adaptor body internal lumen wall to the other side of the internal lumen wall of said adaptor body, reaching fully across the internal lumen wall of said adaptor body, and
wherein said port adaptor comprises a plurality of said at least one elastomeric band arranged in a crossing pattern.

2. The port adaptor of claim 1, wherein said plurality of said at least one elastomeric band are placed vertically to the longitudinal axis along an interior body of the port adaptor.

3. The port adaptor of claim 1, wherein said plurality of said at least one elastomeric band are arranged in a grate pattern.

4. The port adaptor of claim 1, wherein at least two of said plurality of said at least one elastomeric band cross one another.

5. The port adaptor of claim 1, wherein said at least one elastomeric band is made from rubber or silicone.

6. The port adaptor of claim 1, wherein said port adaptor includes a bulge, a proximal arm (615), or any combination thereof, for securing said port adaptor to a trocar.

7. The port adaptor of claim 1, wherein said port adaptor is sized and configured for placement inside a cannula of a trocar.

8. The port adaptor of claim 7, wherein said port adaptor does not protrude out of a distal opening of said trocar.

9. The port adaptor of claim 7, wherein said port adaptor is protrudable out of said trocar cannula, and said plurality of said at least one elastomeric band are presentable out of said trocar cannula.

10. The port adaptor of claim 9, wherein said plurality of said at least one elastomeric band are connected to arms (500-530) and form a stretchable spatial grid.

11. The port adaptor of claim 10, wherein said arms (500-530) are configured to
(a) bend inward when said port adaptor is inserted into said trocar cannula, where inward is towards a center line of a longitudinal axis of said port adaptor;
(b) bend inward when said port adaptor is extracted from said trocar cannula; and
(c) when an endoscope is passed through said arms (500-530), said arms (500-530) bend outward, where outward is away from said center line of said longitudinal axis of said port adaptor, said at least one elastomeric band is configured to clean a lens of said endoscope, and said at least one elastomeric band is configured to clean said endoscopic lens and a slit between said arms (500-530) is enlarged, allowing blood and other wiped material to be ejected through said slit.

12. The port adaptor of claim 1, wherein said port adaptor is sized and configured for placement through a proximal opening of a trocar.

13. The port adaptor of claim 12, wherein said port adaptor includes a proximal housing.

14. The port adaptor of claim 13, wherein said proximal housing comprises a valve.

15. The port adaptor of claim 13, wherein said proximal housing comprises a hose, extending out of said proximal housing.

16. The port adaptor of claim 12, wherein said port adaptor is protrudable out of said trocar, and said plurality of said at least one elastomeric band are presentable out of said trocar.

17. The port adaptor of claim 16, wherein said plurality of said at least one elastomeric band are connected to arms (500-530) and form a stretchable spatial grid.

18. The port adaptor of claim 17, wherein said arms (500-530) are configured to (a) bend inward when said port adaptor is inserted into said trocar cannula, where inward is towards a center line of a longitudinal axis of said port adaptor;

(b) bend inward when said port adaptor is extracted from said trocar cannula; and (c) when an endoscope is passed through said arms (500-530), said arms (500-530) bend outward, where outward is away from said center line of said longitudinal axis of said port adaptor, said at least one elastomeric band is configured to clean a lens of said endoscope, and said at least one elastomeric band is configured to clean said endoscopic lens and a slit between said arms (500-530) is enlarged, allowing blood and other wiped material to be ejected through said slit.

19. The port adaptor of claim 12, wherein said port adaptor does not protrude out of a distal opening of said trocar.

* * * * *